US011267858B2

(12) United States Patent
Bhat et al.

(10) Patent No.: US 11,267,858 B2
(45) Date of Patent: Mar. 8, 2022

(54) METHODS OF TREATMENT USING G-CSF PROTEIN COMPLEX

(71) Applicant: Spectrum Pharmaceuticals, Inc., Irvine, CA (US)

(72) Inventors: Gajanan Bhat, Irvine, CA (US); Shanta Chawla, Irvine, CA (US)

(73) Assignee: Spectrum Pharmaceuticals, Inc., Irvine, CA (US)

( * ) Notice: Subject to any disclaimer, the term of this patent is extended or adjusted under 35 U.S.C. 154(b) by 0 days.

(21) Appl. No.: 16/428,351

(22) Filed: May 31, 2019

(65) Prior Publication Data

US 2020/0377567 A1    Dec. 3, 2020

(51) Int. Cl.
| | | |
|---|---|---|
| C07K 14/535 | (2006.01) | |
| A61K 47/68 | (2017.01) | |
| A61K 38/00 | (2006.01) | |

(52) U.S. Cl.
CPC ........ *C07K 14/535* (2013.01); *A61K 47/6811* (2017.08); *A61K 38/00* (2013.01)

(58) Field of Classification Search
CPC .............................. C07K 14/535; A61K 47/68
See application file for complete search history.

(56) References Cited

U.S. PATENT DOCUMENTS

| | | | |
|---|---|---|---|
| 5,773,581 | A | 6/1998 | Camble et al. |
| 9,421,244 | B2 | 8/2016 | Kim et al. |
| 2004/0265973 | A1 | 12/2004 | Sun et al. |
| 2008/0254512 | A1 | 10/2008 | Capon |
| 2008/0279812 | A1 | 11/2008 | Boyd et al. |
| 2010/0120666 | A1 | 5/2010 | Zopf et al. |
| 2010/0227818 | A1 | 9/2010 | Bock et al. |
| 2012/0294829 | A1 | 11/2012 | Lee et al. |
| 2018/0326013 | A1 | 11/2018 | Kim et al. |
| 2020/0038395 | A1 | 2/2020 | Mohanlal et al. |

FOREIGN PATENT DOCUMENTS

| | | | |
|---|---|---|---|
| WO | 02/28896 A1 | 4/2002 | |
| WO | 2010/061269 A2 | 6/2010 | |
| WO | WO 2014/193173 | * 12/2014 | ........... A61K 38/193 |

OTHER PUBLICATIONS

Lakhnpal et al. (Breast Cancer Manage. 2(5) 367-374, 2013).*
Vanz et al., "Human granulocyte colony stimulating factor (hG-CSF): cloning, overexpression, purification and characterization". Microbial Cell Factories, 2008, vol. 7, article 13, p. 1-12.
Crawford J, Dale DC, Lyman GH. Chemotherapy-induced neutropenia: risks, consequences, and new directions for its management. Cancer. 2004;100(2):228-237.
Dale DC. The discovery, development and clinical applications of granulocyte colony-stimulating factor. Trans Am Clin Climatol Assoc. 1998;109:27-36; discussion 36-28.
Welte K, Gabrilove J, Bronchud MH, Platzer E, Morstyn G Filgrastim (r-metHuG-CSF): the first 10 years. Blood. 1996;88(6):1907-1929.
National Comprehensive Cancer Network. Hematopoietic Growth Factors. National Comprehensive Cancer Network Web site, https://www.nccn.org/professionals/physician_gls/pdf/growthfactors.pdf. Published 2020. Accessed Mar. 25, 2020, 2020.
Arvedson T, O'Kelly J, Yang BB. Design Rationale and Development Approach for Pegfilgrastim as a Long-Acting Granulocyte Colony-Stimulating Factor. Biodrugs. 2015;29(3):185-198.
Molineux G. The design and development of pegfilgrastim (PEG-rmetHuG-CSF, Neulasta). Curr Pharm Des. 2004; 10(11):1235-1244. (abstract only).
Smith TJ, Bohlke K, Lyman GH, et al. Recommendations for the Use of WBC Growth Factors: American Society of Clinical Oncology Clinical Practice Guideline Update J Clin Oncol. 2015;33(28):3199-3212 (abstract only).
Shin KH, Kim TE, Lim KS, et al. Pharmacokinetic and pharmacodynamic properties of a new long-acting granulocyte colony-stimulating factor (HM10460A) in healthy volunteers. Biodrugs. 2013;27(2):149-158. (abstract only).
Rath T, Baker K, Pyzik M, Blumberg RS. Regulation of Immune Responses by the Neonatal Fc Receptor and Its Therapeutic Implications. Front Immunol. 2015;5(664).
Strohl WR. Fusion Proteins for Half-Life Extension of Biologies as a Strategy to Make Biobetters. Biodrugs. 2015;29(4):215-239.
Roopenian DC, Akilesh S. FcRn: the neonatal Fc receptor comes of age. Nat Rev Immunol. 2007;7(9):715-725. (abstract only).
Iwamoto H, Izumi K, Natsagdorj A, et al. Effectiveness and Safety of Pegfilgrastim in BEP Treatment for Patients with Germ Cell Tumor. In Vivo. 2018;32(4):899-903.
Praetor A, Ellinger I, Hunziker W. Intracellular traffic of the MHC class I-like IgG Fc receptor, FcRn, expressed in epithelial MDCK cells J Cell Sci. 1999;112 ( Pt 14):2291-2299.
Bendall LJ, Bradstock KF. G-CSF: From granulopoietic stimulant to bone marrow stem cell mobilizing agent. Cytokine Growth Factor Rev. 2014;25(4):355-367.
Vidarsson G, Dekkers G, Rispens T. IgG subclasses and allotypes: from structure to effector functions. Front Immunol. 2014;5:520.
Hayes JM, Frostell A, Karlsson R, et al. Identification of Fc Gamma Receptor Glycoforms That Produce Differential Binding Kinetics for Rituximab. Mol Cell Proteomics. 2017;16(10):1770-1788.

(Continued)

*Primary Examiner* — Gyan Chandra
(74) *Attorney, Agent, or Firm* — Fox Rothschild LLP

(57) ABSTRACT

This disclosure provides a method of preventing, alleviating, or treating a condition (i.e., neutropenia) in a patient in need thereof, the condition characterized by compromised white blood cell production in the patient. The method includes administering to the patient a therapeutically effective amount of a protein complex comprising a modified human granulocyte-colony stimulating factor (hG-CSF) covalently linked to an immunoglobulin Fc region via a non-peptidyl polymer. The non-peptidyl polymer is site-specifically linked to an N-terminus of the immunoglobulin Fc region, and the modified hG-CSF comprises substitutions in at least one of Cys17 and Pro65.

21 Claims, 3 Drawing Sheets
Specification includes a Sequence Listing.

(56) References Cited

OTHER PUBLICATIONS

Antohe F, Radulescu L, Gafencu A, Ghetie V, Simionescu M. Expression of functionally active FcRn and the differentiated bidirectional transport of IgG in human placental endothelial cells. Hum Immunol. 2001;62(2):93-105. (abstract only).

Rath T, Kuo TT, Baker K, et al. The immunologic functions of the neonatal Fc receptor for IgG. J Clin Immunol. 2013;33 Suppl 1:S9-17.

Jacene HA, Ishimori T, Engles JM, Leboulleux S, Stearns V, Wahl RL. Effects of pegfilgrastim on normal biodistribution of 18F-FDG: preclinical and clinical studies. J Nucl Med. 2006;47(6):950-956.

Morstyn G, Foote MA, Walker T, Molineux G. Filgrastim (r-metHuG-CSF) in the 21st century: SD/01. Acta Haematol. 2001; 105(3):151-155. (abstract only).

Harbeck N, Wang J, Otto GP, Gattu S, Krendyukov A. Safety analysis of proposed pegfilgrastim biosimilar in Phase I and Phase III studies. Future Oncol 2019;15(12):1313-1322.

Waller CF, Ranganna GM, Pennella EJ, et al. Randomized phase 3 efficacy and safety trial of proposed pegfilgrastim biosimilar MYL-1401H in the prophylactic treatment of chemotherapy-induced neutropenia. Ann Hematol. 2019;98(5):1217-1224.

Kim SK, Demetri GD. Chemotherapy and neutropenia. Hematol Oncol Clin North Am. 1996;10(2):377-395. (abstract only).

Weycker D, Li X, Figueredo J, Barron R, Tzivelekis S, Hagiwara M. Risk of chemotherapy-induced febrile neutropenia in cancer patients receiving pegfilgrastim prophylaxis: does timing of adminisliation matter? Support Care Cancer. 2016;24(5):2309-2316.

Burris HA, Belani CP, Kaufman PA, et al. Pegfilgrastim on the Same Day Versus Next Day of Chemotherapy in Patients With Breast Cancer, Non-Small-Cell Lung Cancer, Ovarian Cancer, and Non-Hodgkin's Lymphoma: Results of Four Multicenter, Double-Blind, Randomized Phase II Studies. J Oncol Pract. 2010;6(3):133-140.

Scholz M, Engel C, Apt D, Sankar SL, Goldstein E, Loeffler M. Pharmacokinetic and pharmacodynamic modelling of the novel human granulocyte colony-stimulating factor derivative Maxy-G34 and pegfilgrastim in rats. Cell Prolif. 2009;42(6):823-837.

Ishikawa et al. "The Substitution of Cysteine 17 of Recombinant Human G-CSF with Alanine Greatly Enhanced its Stability," Cell Structure and Function, Feb. 28, 1992 (Feb. 28, 1992) vol. 17, No. 1, pp. 61-65.

International Search Report and Written Opinion dated Dec. 17, 2021, in related International Application No. PCT/US2021/046108, 12 pages.

\* cited by examiner

A

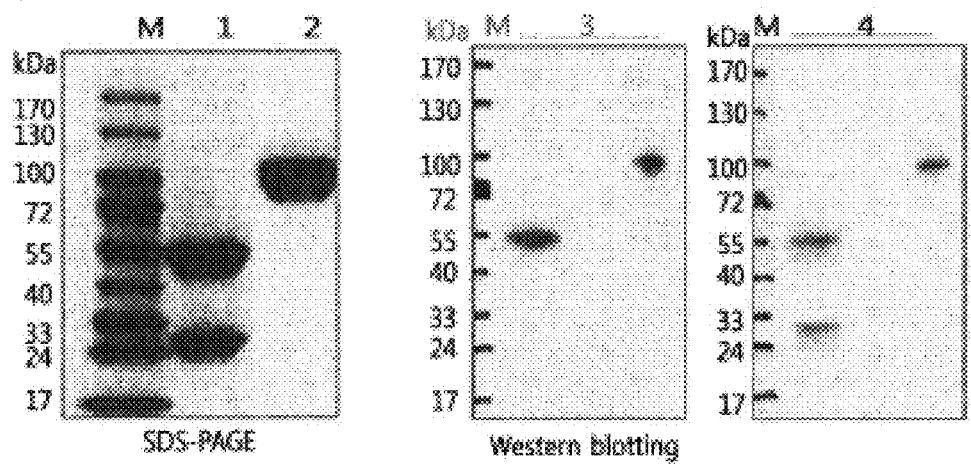

M. Size Marker
1. hGH-PEG-Fc reducing conditions
2. hGH-PEG-Fc non-reducing conditions
3. Use of anti-hGH antibody (hGH-PEG-Fc reducing, non-reducing conditions)
4. Use of anti-Fc antibody (hGH-PEG-Fc reducing, non-reducing conditions)

B

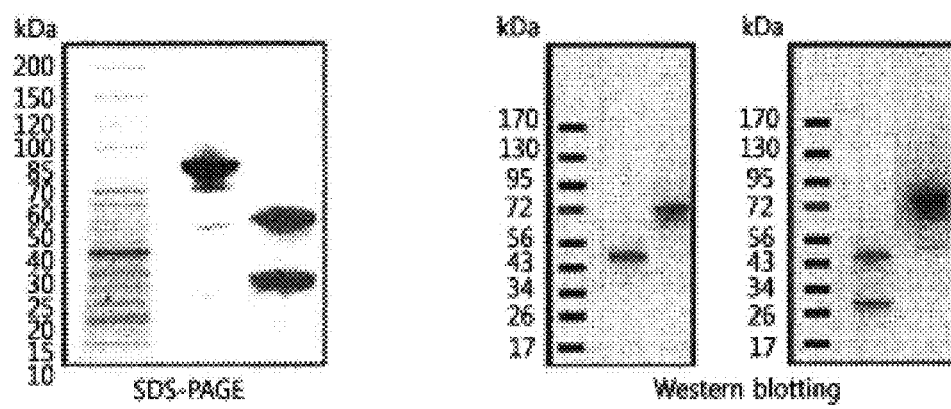

M. Size Marker
1. $^{17,65}$Ser-G-CSF-PEG-Fc non-reducing conditions
2. $^{17,65}$Ser-G-CSF-PEG-Fc reducing conditions
3. Use of anti-G-CSF antibody
($^{17,65}$Ser-G-CSF-PEG-Fc reducing, non-reducing conditions)
4. Use of anti-Fc antibody
($^{17,65}$Ser-G-CSF-PEG-Fc reducing, non-reducing conditions)

FIGS. 1A and 1B

SEQUENCE LISTING

```
<160> NUMBER OF SEQ ID NOS: 2

<210> SEQ ID NO 1
<211> LENGTH: 174
<212> TYPE: PRT
<213> ORGANISM: Homo sapiens

<400> SEQUENCE: 1
```

```
Thr Pro Leu Gly Pro Ala Ser Ser Leu Pro Gln Ser Phe Leu Leu Lys
1               5                   10                  15

Ser Leu Glu Gln Val Arg Lys Ile Gln Gly Asp Gly Ala Ala Leu Gln
            20                  25                  30

Glu Lys Leu Cys Ala Thr Tyr Lys Leu Cys His Pro Glu Glu Leu Val
        35                  40                  45

Leu Leu Gly His Ser Leu Gly Ile Pro Trp Ala Pro Leu Ser Ser Cys
    50                  55                  60

Ser Ser Gln Ala Leu Gln Leu Ala Gly Cys Leu Ser Gln Leu His Ser
65              70                  75                  80

Gly Leu Phe Leu Tyr Gln Gly Leu Leu Gln Ala Leu Glu Gly Ile Ser
                85                  90                  95

Pro Glu Leu Gly Pro Thr Leu Asp Thr Leu Gln Leu Asp Val Ala Asp
            100                 105                 110

Phe Ala Thr Thr Ile Trp Gln Gln Met Glu Glu Leu Gly Met Ala Pro
            115                 120                 125

Ala Leu Gln Pro Thr Gln Gly Ala Met Pro Ala Phe Ala Ser Ala Phe
        130                 135                 140

Gln Arg Arg Ala Gly Gly Val Leu Val Ala Ser His Leu Gln Ser Phe
145                 150                 155                 160

Leu Glu Val Ser Tyr Arg Val Leu Arg His Leu Ala Gln Pro
                165                 170

<210> SEQ ID NO 2
<211> LENGTH: 221
<212> TYPE: PRT
<213> ORGANISM: Homo sapiens

<400> SEQUENCE: 2

Pro Ser Cys Pro Ala Pro Glu Phe Leu Gly Gly Pro Ser Val Phe Leu
1               5                   10                  15

Phe Pro Pro Lys Pro Lys Asp Thr Leu Met Ile Ser Arg Thr Pro Glu
            20                  25                  30

Val Thr Cys Val Val Val Asp Val Ser Gln Glu Asp Pro Glu Val Gln
        35                  40                  45

Phe Asn Trp Tyr Val Asp Gly Val Glu Val His Asn Ala Lys Thr Lys
    50                  55                  60

Pro Arg Glu Glu Gln Phe Asn Ser Thr Tyr Arg Val Val Ser Val Leu
65              70                  75                  80

Thr Val Leu His Gln Asp Trp Leu Asn Gly Lys Glu Tyr Lys Cys Lys
                85                  90                  95

Val Ser Asn Lys Gly Leu Pro Ser Ser Ile Glu Lys Thr Ile Ser Lys
            100                 105                 110

Ala Lys Gly Gln Pro Arg Glu Pro Gln Val Tyr Thr Leu Pro Pro Ser
        115                 120                 125

Gln Glu Glu Met Thr Lys Asn Gln Val Ser Leu Thr Cys Leu Val Lys
        130                 135                 140

Gly Phe Tyr Pro Ser Asp Ile Ala Val Glu Trp Glu Ser Asn Gly Gln
145                 150                 155                 160

Pro Glu Asn Asn Tyr Lys Thr Thr Pro Pro Val Leu Asp Ser Asp Gly
                165                 170                 175

Ser Phe Phe Leu Tyr Ser Arg Leu Thr Val Asp Lys Ser Arg Trp Gln
            180                 185                 190
```

```
Glu Gly Asn Val Phe Ser Cys Ser Val Met His Glu Ala Leu His Asn
        195                 200                 205

His Tyr Thr Gln Lys Ser Leu Ser Leu Ser Leu Gly Lys
    210                 215                 220
```

METHODS OF TREATMENT USING G-CSF PROTEIN COMPLEX

TECHNICAL FIELD

The present invention relates to protein complexes, pharmaceutical compositions, and methods of use thereof for treating, preventing, or reducing the risk of developing a condition, such as neutropenia. The protein complex can be formed by linking an immunoglobulin Fc region to a physiologically active polypeptide via a non-peptidyl polymer, in which the non-peptidyl polymer is linked to the immunoglobulin Fc region.

BACKGROUND OF THE INVENTION

Neutropenia is a relatively common disorder most often associated with chemotherapy treatments, adverse drug reactions, or autoimmune disorders. Chemotherapy-induced neutropenia is common toxicity caused by the administration of anticancer drugs. It is associated with life-threatening infections and may alter the chemotherapy schedule, thus impacting on early and long-term clinical outcome. Febrile Neutropenia is major dose-limiting toxicity of myelosuppressive chemotherapy regimens such as docetaxel, doxorubicin, cyclophosphamide (TAC); dose-dense doxorubicin plus cyclophosphamide (AC), with or without subsequent weekly or semiweekly paclitaxel; and docetaxel plus cyclophosphamide (TC). It usually leads to prolonged hospitalization, intravenous administration of broad-spectrum antibiotics, and is often associated with significant morbidity and mortality. About 25% to 40% of treatment naïve patients develop febrile neutropenia with common chemotherapy regimens in the absence of G-CSF support.

Current therapeutic modalities employ granulocyte colony-stimulating factor (G-CSF) and/or antibiotic agents to combat this condition. However, G-CSF or its other polypeptide derivatives are easy to denature or easily decomposed by proteolytic enzymes in blood to be readily removed through the kidney or liver. Therefore, to maintain the blood concentration and titer of the G-CSF containing drugs, it is necessary to frequently administer the protein drug to patients, which causes excessive suffering in patients. To solve such problems, G-CSF was chemically attached to polymers having a high solubility such as polyethylene glycol ("PEG"), thereby increasing its blood stability and maintaining suitable blood concentration for a longer time.

However, binding of PEG to G-CSF, even though may increase blood stability, does dramatically reduce the titer needed for optimal physiologic effect. Thus there is a need to address this shortcoming in the art.

Thus, there is a strong need for new formulations and methods of use where the new G-CSF containing protein complex can stay stable and dramatically improve patient outcome.

SUMMARY OF THE INVENTION

The present invention is directed to methods of using a G-CSF containing a more stable protein complex that can be easily prepared and administered to patients at risk of developing neutropenia, and maintain a serum concentration that achieves the optimal therapeutic outcome. Another aspect of the present invention is directed to a protein complex prepared by linking a physiologically active polypeptide and an immunoglobulin Fc fragment via a non-peptidyl polymer, in which the non-peptidyl polymer is site-specifically linked to an N-terminus of the immunoglobulin Fc fragment.

In one aspect, this disclosure provides a method of preventing, alleviating or treating a condition in a patient in need thereof. The method comprises administering to the patient a therapeutically effective amount of a protein complex comprising a modified human granulocyte-colony stimulating factor (hG-CSF) covalently linked to an immunoglobulin Fc region via a non-peptidyl polymer, wherein the non-peptidyl polymer is site-specifically linked to an N-terminus of the immunoglobulin Fc region and the modified hG-CSF comprises substitutions in at least one of Cys17 and Pro65.

The condition is characterized by compromised white blood cell production in the patient. For example, the condition can be one of: reduced hematopoietic function, reduced immune function, reduced neutrophil count, reduced neutrophil mobilization, mobilization of peripheral blood progenitor cells, sepsis, severe chronic neutropenia, febrile neutropenia, bone marrow transplants, infectious diseases, leucopenia, thrombocytopenia, anemia, enhancing engraftment of bone marrow during transplantation, enhancing bone marrow recovery in treatment of radiation, chemical or chemotherapeutic induced bone marrow aplasia or myelosuppression, and acquired immune deficiency syndrome.

In some embodiments, the condition can be severe chronic neutropenia. In some embodiments, the condition can be febrile neutropenia. In some embodiments, compromised white blood cell production can be a result of chemotherapy, radiation therapy, or idiopathic thrombocytopenia purpura.

In some embodiments, the protein complex can be administered after the patient is treated with adjuvant or neoadjuvant chemotherapy. In some embodiments, the protein complex can be administered between 1 and 5 days after the patient is treated with adjuvant or neoadjuvant chemotherapy. In some embodiments, the adjuvant or neoadjuvant chemotherapy can be a combination of docetaxel and cyclophosphamide.

In some embodiments, a second dose of the protein complex can be administered between 15 and 25 days after a first dose of the protein complex is administered to the patient.

In some embodiments, the therapeutically effective amount is a unit dosage form selected from: 25 µg/kg, 50 µg/kg, 100 µg/kg, and 200 µg/kg. In some embodiments, the therapeutically effective amount is 13.2 mg of the protein complex in a 0.6 mL dosage volume.

In some embodiments, the method further comprises administering to the patient a therapeutically effective amount of a second agent (e.g., an anti-cancer agent).

In some embodiments, the substitution at Cys17 can be Cys17Ser, and the substitution at Pro65 can be Pro65Ser.

In some embodiments, the modified human G-CSF comprises a polypeptide sequence of SEQ ID NOs: 1. In some embodiments, the immunoglobulin Fc region comprises a polypeptide sequence of SEQ ID NO: 2.

In some embodiments, both ends of the non-peptidyl polymer are respectively linked to the modified human G-CSF and the immunoglobulin Fc region through reactive groups by a covalent bond.

In some embodiments, the immunoglobulin Fc region can be characterized by: (a) the immunoglobulin Fc region is aglycosylated; (b) the immunoglobulin Fc region consists of CH2 and CH3 domains; (c) the immunoglobulin Fc region comprises one of CH2, CH3, and CH4 domains; (d) the immunoglobulin Fc region further comprises a hinge region; or (e) the immunoglobulin Fc region is an immunoglobulin Fc fragment derived from IgG, IgA, IgD, IgE, or IgM.

In some embodiments, the immunoglobulin Fc region can be further characterized by: (a) each domain of the immunoglobulin Fc fragment is a hybrid of domains, in which each domain has a different origin derived from immunoglobulins selected from the group consisting of IgG, IgA, IgD, IgE, and IgM; (b) the immunoglobulin Fc fragment is a dimer or multimer consisting of single chain immunoglobulins comprising domains having the same origin; (c) the immunoglobulin Fc fragment is an IgG4 Fc fragment; or (d) the immunoglobulin Fc fragment is a human aglycosylated IgG4 Fc fragment.

In some embodiments, the non-peptidyl polymer is: (a) selected from the group consisting of polyethylene glycol, polypropylene glycol, an ethylene glycol-propylene glycol copolymer, polyoxyethylated polyol, polyvinyl alcohol, polysaccharide, dextran, polyvinyl ethyl ether, a biodegradable polymer, a lipid polymer, chitin, hyaluronic acid, and a combination thereof; or (b) polyethylene glycol. In some embodiments, the polyethylene glycol has a molecular weight of 3.4 kDa.

In some embodiments, the reactive group of the non-peptidyl polymer is selected from the group consisting of an aldehyde group, a maleimide group, and a succinimide derivative. For example, the aldehyde group can be a propionaldehyde group or a butyraldehyde group. The succinimide derivative can be succinimidyl carboxymethyl, succinimidyl valerate, succinimidyl methylbutanoate, succinimidyl methylpropionate, succinimidyl butanoate, succinimidyl propionate, N-hydroxysuccinimide, or succinimidyl carbonate.

In some embodiments, the non-peptidyl polymer has an aldehyde group as a reactive group at both ends. In some embodiments, the non-peptidyl polymer has an aldehyde group and a maleimide group as a reactive group at both ends, respectively. In some embodiments, the non-peptidyl polymer has an aldehyde group and a succinimide group as a reactive group at both ends, respectively.

In some embodiments, each end of the non-peptidyl polymer is linked to the N-terminus of the immunoglobulin Fc region and an N-terminus, a C-terminus, or a free reactive group of a lysine residue, a histidine residue, or a cysteine residue of the modified human G-CSF, respectively.

In another aspect, this disclosure provides a method for treating or preventing neutropenia in a patient receiving chemotherapy. The method comprises comprising administering to said patient a protein complex comprising a physiologically active polypeptide linked to an immunoglobulin Fc region via a non-peptidyl polymer, wherein the non-peptidyl polymer is site-specifically linked to an N-terminus of the immunoglobulin Fc region. In some embodiments, the physiologically active polypeptide is G-CSF.

In some embodiments, both ends of the non-peptidyl polymer is respectively linked to the physiologically active polypeptide and the immunoglobulin Fc region through reactive groups by a covalent bond.

In some embodiments, the immunoglobulin Fc region is an immunoglobulin. In some embodiments, the immunoglobulin Fc region is aglycosylated. In some embodiments, the immunoglobulin Fc region comprises any one of CH2, CH3, and CH4 domains. In some embodiments, the immunoglobulin Fc region consists of CH2 and CH3 domains. The immunoglobulin Fc region can further comprise a hinge region.

In some embodiments, each domain of the immunoglobulin Fc fragment is a hybrid of domains, in which each domain has a different origin derived from immunoglobulins selected from the group consisting of IgG, IgA, IgD, IgE, and IgM.

In some embodiments, the protein complex can be administered to the patient within about 6 hours, about 5 hours, 2 hours, or 1 hour of the completion of chemotherapy.

In another aspect, the present invention provides a method of preparing the protein complex in a pharmaceutical composition for improving in vivo duration and stability of the physiologically active polypeptide, the composition including the protein complex as an active ingredient.

BRIEF DESCRIPTION OF THE DRAWINGS

FIG. 1A shows results of SDS-PAGE and western blotting of a $^{17,65}$Ser-G-CSF-PEG-Fc complex which was prepared by N-terminal reaction of an immunoglobulin Fc region.

FIG. 1B shows a result of peptide mapping for analyzing Fc region N-terminal binding of a $^{17,65}$Ser-G-CSF-PEG-Fc complex which was prepared by N-terminal reaction of an immunoglobulin Fc region.

DETAILED DESCRIPTION OF THE INVENTION

Figure 2:
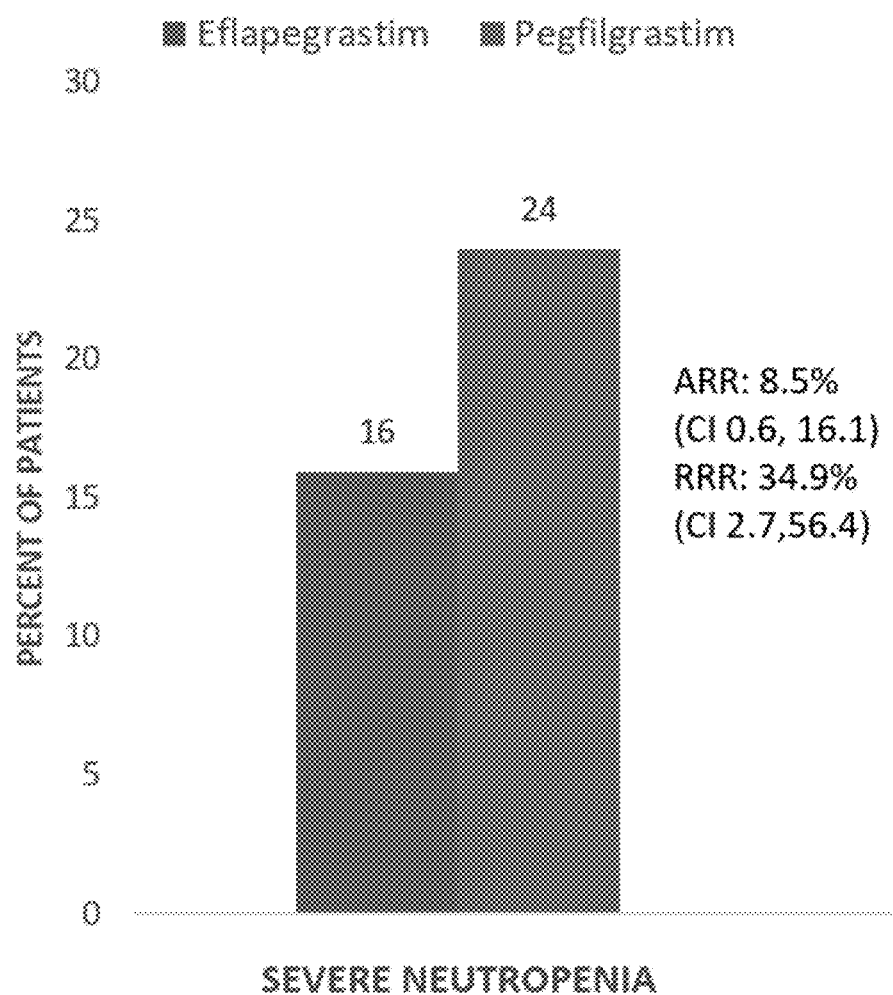
FIG. 2 shows that the reduction in the incidence of severe neutropenia in the $^{17,65}$Ser-G-CSF-PEG-Fc (EFLAPEGRASTIM) arm that is statistically significant.

Broadly speaking, the present disclosure provides methods of preventing, alleviating, prophylactically treating, and treating a patient having a condition characterized by the compromised white blood cell production. The method includes administering to the patient in need of such treatment a therapeutically effective amount of a protein complex comprising a physiologically active polypeptide, such as a modified human granulocyte-colony stimulating factor (hG-CSF), covalently linked to an immunoglobulin Fc region via a non-peptidyl polymer. The non-peptidyl polymer can be site-specifically linked to an N-terminus of the immunoglobulin Fc region, and the modified hG-CSF includes substitutions in at least one of Cys17 and Pro65.

In another aspect, the present disclosure provides a method for increasing the number of granulocytes in eligible patients for a bone marrow transplant. The method includes administering to the patient in need of such treatment a therapeutically effective amount of a protein complex comprising a modified human granulocyte-colony stimulating factor (hG-CSF) covalently linked to an immunoglobulin Fc region via a non-peptidyl polymer, wherein the non-peptidyl polymer is site-specifically linked to an N-terminus of the immunoglobulin Fc region and the modified hG-CSF comprises substitutions in at least one of Cys17 and Pro65.

In yet another aspect, the present disclosure provides a method for increasing stem cell production in a patient. The method includes administering to the patient in need of such treatment a therapeutically effective amount of a protein complex comprising a modified human granulocyte-colony stimulating factor (hG-CSF) covalently linked to an immunoglobulin Fc region via a non-peptidyl polymer, wherein the non-peptidyl polymer is site-specifically linked to an N-terminus of the immunoglobulin Fc region and the modified hG-CSF comprises substitutions in at least one of Cys17 and Pro65.

In yet another aspect, the present disclosure provides a method for increasing the number of hematopoietic progenitor cells in a patient in need that include those undergoing chemotherapy or those who are donors of stem cells to other patients. The method includes administering to the patient a therapeutically effective amount of a protein conjugate comprising a modified human granulocyte-colony stimulating factor (hG-CSF) covalently linked to an immunoglobulin Fc region via a non-peptidyl polymer, wherein the non-peptidyl polymer is site-specifically linked to an N-terminus of the immunoglobulin Fc region and the modified hG-CSF comprises substitutions in at least one of Cys17 and Pro65.

In some embodiments, the conditions to be treated include reduced hematopoietic function, reduced immune function, reduced neutrophil count, reduced neutrophil mobilization, mobilization of peripheral blood progenitor cells, sepsis, severe chronic neutropenia, bone marrow transplants, infectious diseases, leucopenia, thrombocytopenia, anemia, enhancing engraftment of bone marrow during transplantation, enhancing bone marrow recovery in treatment of radiation, chemical or chemotherapeutic induced bone marrow aplasia or myelosuppression, and acquired immune deficiency syndrome. In one embodiment, the condition is a myelosuppression, neutropenia, or preferably febrile neutropenia.

In another aspect, the present disclosure provides a method for preventing, alleviating, prophylactically treating, and treating infection as manifested by neutropenia (e.g., febrile neutropenia) in the patient with non-myeloid malignancies receiving myelosuppressive anticancer drugs. The method includes administering to the patient a therapeutically effective amount of a protein complex comprising a modified human granulocyte-colony stimulating factor (hG-CSF) covalently linked to an immunoglobulin Fc region via a non-peptidyl polymer, wherein the non-peptidyl polymer is site-specifically linked to an N-terminus of the immunoglobulin Fc region and the modified hG-CSF comprises substitutions in at least one of Cys17 and Pro65.

In some embodiments, the compromised white blood cell production is a result of chemotherapy, radiation therapy, adjuvant or neoadjuvant chemotherapy, or idiopathic thrombocytopenia purpura. In certain embodiments, the adjuvant or neoadjuvant chemotherapy is a combination of docetaxel and cyclophosphamide. In other embodiments, the therapeutic effective amount is a unit dosage form selected from: 25 μg/kg, 50 μg/kg, 100 μg/kg, and 200 μg/kg. In certain embodiments, the present methodology, further includes administering to the patient a therapeutically effective amount of a second agent, such as an anti-cancer agent. In certain embodiments, the modified G-CSF is by way of a substitution at Cys17 is Cys17Ser. In other embodiments, the substation at Pro65 is Pro65Ser.

In some embodiments, the immunoglobulin Fc region comprises a polypeptide sequence of SEQ ID NO: 1. In some embodiments, the modified G-CSF comprises a polypeptide sequence of SEQ ID NO: 2.

| SEQ ID NO | SEQUENCE | OTHER INFORMATION |
|---|---|---|
| SEQ ID NO: 1 | TPLGPASSLPQSFLLKSLEQVR KIQGDGAALQEKLCATYKLCHP EELVLLGHSLGIPWAPLSSCSS QALQLAGCLSQLHSGLFLYQGL LQALEGISPELGPTLDTLQLDV ADFATTIWQQMEELGMAPALQP TQGAMPAFASAFQRRAGGVLVA SHLQSFLEVSYRVLRHLAQP | G-CSF (17Ser and 65Ser) |
| SEQ ID NO: 2 | PSCPAPEFLGGPSVFLFPPKPK DTLMISRTPEVTCVVVDVSQED PEVQFNWYVDGVEVHNAKTKPR EEQFNSTYRVVSVLTVLHQDWL NGKEYKCKVSNKGLPSSIEKTI SKAKGQPREPQVYTLPPSQEEM TKNQVSLTCLVKGFYPSDIAVE WESNGQPENNYKTTPPVLDSDG SFFLYSRLTVDKSRWQEGNVFS CSVMHEALHNHYTQKSLSLSLG K | Immunoglobulin Fc region (IgG4) |

In some embodiments, the protein complex employed in the present methods contain (a) each domain of the immunoglobulin Fc fragment is a hybrid of domains, in which each domain has a different origin derived from immunoglobulins selected from the group consisting of IgG, IgA, IgD, IgE, and IgM; (b) the immunoglobulin Fc fragment is a dimer or multimer consisting of single chain immunoglobulins comprising domains having the same origin; (c) the immunoglobulin Fc fragment is an IgG4 Fc fragment; or (d) the immunoglobulin Fc fragment is a human aglycosylated IgG4 Fc fragment.

In certain embodiments, the non-peptidyl polymer is selected from the group consisting of polyethylene glycol, polypropylene glycol, an ethylene glycol-propylene glycol copolymer, polyoxyethylated polyol, polyvinyl alcohol, polysaccharide, dextran, polyvinyl ethyl ether, a biodegradable polymer, a lipid polymer, chitin, hyaluronic acid, and a combination thereof. In a preferred embodiment, the non-peptidyl polymer is polyethylene glycol.

In another aspect, the present disclosure provides a method for treating or preventing neutropenia in a patient receiving chemotherapy. The method comprises administering to said patient a protein complex comprising a modified G-CSF linked to an immunoglobulin Fc region via a non-peptidyl polymer, wherein the non-peptidyl polymer is site-specifically linked to an N-terminus of the immunoglobulin Fc region. In some embodiments, both ends of the non-peptidyl polymer are respectively linked to the physiologically active polypeptide and the immunoglobulin Fc region through reactive groups by a covalent bond. In a preferred embodiment, the immunoglobulin Fc region is aglycosylated.

In some embodiments, the G-CSF complex composition is administered to the patient within about 5 hours, 2 hours, 1 hour, or half an hour of the completion of chemotherapy.

In some embodiment, the present invention provides the protein complex in which the immunoglobulin Fc region comprises one of CH2, CH3, and CH4 domains. For example, the immunoglobulin Fc region can include CH2 and CH3 domains. In some embodiments, the immunoglobulin Fc region further includes a hinge region.

In some embodiments, the immunoglobulin Fc region is an immunoglobulin Fc fragment derived from IgG, IgA, IgD, IgE, or IgM. In some embodiments, each domain of the immunoglobulin Fc fragment is a hybrid of domains and each domain has a different origin derived from immunoglobulins selected from the group consisting of IgG, IgA, IgD, IgE, and IgM. In some embodiments, the immunoglobulin Fc fragment is a dimer or multimer consisting of single chain immunoglobulins comprising domains having the same origin. In some embodiments, the immunoglobulin Fc fragment is an IgG4 Fc fragment.

In some embodiments, the non-peptidyl polymer can be one of polyethylene glycol, polypropylene glycol, an ethylene glycol-propylene glycol copolymer, polyoxyethylated polyol, polyvinyl alcohol, polysaccharide, dextran, polyvinyl ethyl ether, a biodegradable polymer, a lipid polymer, chitin, hyaluronic acid, and a combination thereof, preferably the non-peptidyl polymer is polyethylene glycol. In some embodiments, the non-peptidyl polymer is 3.4 kDa polyethylene glycol.

In some embodiments, the reactive group of the non-peptidyl polymer can be one of an aldehyde group, a maleimide group, and a succinimide derivative. The aldehyde group can be a propionaldehyde group or a butyraldehyde group. The succinimide derivative can be succinimidyl carboxymethyl, succinimidyl valerate, succinimidyl methylbutanoate, succinimidyl methylpropionate, succinimidyl butanoate, succinimidyl propionate, N-hydroxysuccinimide, or succinimidyl carbonate.

In some embodiments, the non-peptidyl polymer has an aldehyde group as a reactive group at both ends. In some embodiments, the non-peptidyl polymer has an aldehyde group and a maleimide group as a reactive group at both ends, respectively. In some embodiments, the non-peptidyl polymer has an aldehyde group and a succinimide group as a reactive group at both ends, respectively.

In some embodiments, the present invention provides the protein complex in which each end of the non-peptidyl polymer is linked to the N-terminus of the immunoglobulin Fc region; and the N-terminus, C-terminus, or a free reactive group of a lysine residue, a histidine residue, or a cysteine residue of the physiologically active polypeptide, respectively.

In another aspect, this disclosure provides a method for treating or preventing neutropenia in a patient receiving chemotherapy. The method comprises comprising administering to said patient a protein complex comprising a physiologically active polypeptide linked to an immunoglobulin Fc region via a non-peptidyl polymer, wherein the non-peptidyl polymer is site-specifically linked to an N-terminus of the immunoglobulin Fc region.

In some embodiments, the physiologically active polypeptide can be one of a hormone, a cytokine, an enzyme, an antibody, a growth factor, a transcription factor, a blood coagulation factor, a vaccine, a structural protein, a ligand protein, and a receptor. In some embodiments, the physiologically active polypeptide is G-CSF.

In another aspect, the present disclosure also provides a method of preparing the protein complex. The method comprises:

(a) preparing a protein complex by linking at least one non-peptidyl polymer having a reactive group at both ends, at least one physiologically active polypeptide, and at least one immunoglobulin Fc region by a covalent bond, and (b) isolating the protein complex, essentially including the covalently linked physiologically active polypeptide, non-peptidyl polymer, and immunoglobulin Fc region prepared in step (a), in which the non-peptidyl polymer is linked to the N-terminus of the immunoglobulin Fc fragment.

A specific embodiment of the present invention provides the preparation method, in which step (a) comprises:

(a1) preparing a conjugate by linking one end of the non-peptidyl polymer to the immunoglobulin Fc region or the physiologically active polypeptide by a covalent bond; and (a2) isolating the conjugate prepared in step (a1) and linking the other end of the non-peptidyl polymer of the isolated conjugate to the other of the immunoglobulin Fc region and the physiologically active polypeptide by a covalent bond.

Another specific embodiment of the present invention provides the preparation method in which in step (a1), the reaction mole ratio between the physiologically active polypeptide and the non-peptidyl polymer is in the range from 1:1 to 1:30, and the reaction mole ratio between the immunoglobulin Fc fragment and the non-peptidyl polymer is in the range from 1:1 to 1:20.

Still another specific embodiment of the present invention provides the preparation method in which step (a1) is performed in a pH condition from 4.0 to 9.0.

Still another specific embodiment of the present invention provides the preparation method in which step (a1) is performed at a temperature from 4.0° C. to 25° C.

Still another specific embodiment of the present invention provides the preparation method in which in step (a1), the reaction concentration of the immunoglobulin Fc region or physiologically active polypeptide is in the range from 0.1 mg/mL to 100 mg/mL.

Still another specific embodiment of the present invention provides the preparation method in which in step (a2), the reaction mole ratio between the conjugate and the immunoglobulin Fc region or the physiologically active polypeptide is in the range from 1:0.1 to 1:20.

Still another specific embodiment of the present invention provides the preparation method in which step (a2) is performed in a pH condition from 4.0 to 9.0.

Still another specific embodiment of the present invention provides the preparation method in which step (a2) is performed at a temperature from 4.0° C. to 25° C.

Still another specific embodiment of the present invention provides the preparation method in which in step (a2), the concentration of the immunoglobulin Fc region or physiologically active polypeptide is in the range from 0.1 mg/mL to 100 mg/mL.

Still another specific embodiment of the present invention provides the preparation method in which step (a1) and step (a2) are performed in the presence of a reducing agent.

Still another specific embodiment of the present invention provides the preparation method in which the reducing agent is selected from the group consisting of sodium cyanoborohydride (NaCNBH3), sodium borohydride, dimethylamine borate, and pyridine borate.

Still another specific embodiment of the present invention provides the preparation method in which in step (a2), the isolation is performed by a single or combined purification method selected from the group consisting of anion exchange chromatography, cation exchange chromatography, hydrophobic chromatography, affinity chromatography, and size exclusion chromatography.

Still another specific embodiment of the present invention provides the preparation method in which the functional group of the anion exchange chromatography resin is any one selected from the group consisting of quaternary ammonium (Q), quaternary aminoethyl (QAE), diethylaminoethyl (DEAE), polyethylene amine (PEI), dimethyl-laminomethyl (DMAE), and trimethylaminoethyl (TMAE).

Still another specific embodiment of the present invention provides the preparation method in which the functional group of the cation exchange chromatography resin is any one selected from the group consisting of methylsulfonate (S), sulfopropyl (SP), carboxymethyl (CM), sulfoethyl (SE), and polyaspartic acid.

Still another specific embodiment of the present invention provides the preparation method in which the functional group of the hydrophobic chromatography resin is any one selected from the group consisting of phenyl, octyl, (iso) propyl, butyl, and ethyl.

Still another specific embodiment of the present invention provides the preparation method in which the functional group of the affinity chromatography resin is any one selected from the group consisting of protein A, heparin, blue, benzamidine, metal ions (cobalt, nickel, and copper), and an antibody to a part or the entirety of constituting components of the protein complex, in which both ends of the non-peptidyl polymer are respectively conjugated to the immunoglobulin Fc region and the physiologically active polypeptide.

Still another specific embodiment of the present invention provides the preparation method in which the resin of the size exclusion chromatography is selected from the group consisting of Superdex, Sephacryl, Superpose, and Sephadex.

Still another specific embodiment of the present invention provides the preparation method in which the isolating the protein complex of step (b) is performed by a single or combined method selected from the group consisting of anion exchange chromatography, cation exchange chromatography, hydrophobic chromatography, affinity chromatography, and size exclusion chromatography.

Still another specific embodiment of the present invention provides the preparation method in which the functional group of the anion exchange chromatography resin is any one selected from the group consisting of quaternary ammonium (Q), quaternary aminoethyl (QAE), diethylaminoethyl (DEAE), polyethylene amine (PEI), dimethyl-aminomethyl (DMAE), and trimethylaminoethyl (TMAE).

Still another specific embodiment of the present invention provides the preparation method in which the functional group of the cation exchange chromatography resin is any one selected from the group consisting of methylsulfonate (S), sulfopropyl (SP), carboxymethyl (CM), sulfoethyl (SE), and polyaspartic acid.

Still another specific embodiment of the present invention provides the preparation method in which the functional group of the hydrophobic chromatography resin is any one selected from the group consisting of phenyl, octyl, (iso) propyl, butyl, and ethyl.

Still another specific embodiment of the present invention provides the preparation method in which the functional group of the affinity chromatography resin is any one selected from the group consisting of protein A, heparin, blue, benzamidine, metal ions (cobalt, nickel, and copper), an antibody to a part or the entirety of constituting components of the protein complex, in which both ends of the non-peptidyl polymer are respectively conjugated to the immunoglobulin Fc region and the physiologically active polypeptide.

Still another specific embodiment of the present invention provides the preparation method in which the resin of the size exclusion chromatography is selected from the group consisting of Superdex, Sephacryl, Superpose, and Sephadex.

Still another specific embodiment of the present invention provides the preparation method in which step (b) is to isolate the protein complex in which the non-peptidyl polymer and an immunoglobulin Fc region, constituting a protein complex, are linked through the N-terminus of the immunoglobulin Fc region.

Still another aspect of the present invention provides a method of preparing the position-specific protein complex, the method comprising:

(a') preparing a conjugate by linking one end of the non-peptidyl polymer to the immunoglobulin Fc region or the physiologically active polypeptide by a covalent bond, which is performed in a pH condition from 4.0 to 9.0;

(b') isolating the conjugate prepared in step (a') and linking the other end of the non-peptidyl polymer of the isolated conjugate to the other of the immunoglobulin Fc region and the physiologically active polypeptide by a covalent bond, which is performed in a pH condition from 4.0 to 9.0; and (c') isolating the protein complex, essentially including the covalently linked physiologically active polypeptide, non-peptidyl polymer, and immunoglobulin Fc region prepared in step (b'), in which the non-peptidyl polymer is linked to the N-terminus of the immunoglobulin Fc fragment.

In particular, an important condition for a reaction rate in binding between the non-peptidyl polymer and the N-terminus of the immunoglobulin Fc region is pH, and the site-specific binding may occur well at a pH value below neutral pH, that is, below pH 7.0.

The linking of the non-peptidyl polymer to the N-terminus of the immunoglobulin Fc region is performed at a pH value below neutral pH, but suitably performed at a weak acidic to acidic pH which does not denature a tertiary structure or activity of the protein, but is not limited thereto. As a non-limiting example, the immunoglobulin Fc region used in the present invention has an amino acid sequence of SEQ ID NO: 2, and it was confirmed to have N-terminal specificity at a weak basic condition of about pH 8.2 (Example 5).

That is, when a general immunoglobulin Fc region is used, the reaction rate of specific binding of N-terminal of the immunoglobulin Fc region and the non-peptidyl polymer is increased at a pH below neutral pH. However, when an immunoglobulin Fc region mutated to have a lower pH sensitivity is used, the reaction rate of the binding may not be restricted to the condition.

Still another aspect of the present invention provides a method of preparing the protein complex, the method comprising:

(a') preparing a conjugate by linking one end of the non-peptidyl polymer to any one of the immunoglobulin Fc region and the physiologically active polypeptide by a covalent bond, in which the reaction mole ratio between the physiologically active polypeptide and the non-peptidyl polymer is in the range from 1:1 to 1:30, and the reaction mole ratio between the immunoglobulin Fc region and the non-peptidyl polymer is in the range from 1:1 to 1:20, a reducing agent is contained in the range from 1 mM to 100 mM, and the reaction is performed in the condition of pH from 4.0 to 9.0, at a temperature from 4.0° C. to 25° C., and the reaction concentration of the immunoglobulin Fc region or physiologically active polypeptide is in the range from 0.1 mg/mL to 100 mg/mL;

(b') isolating the conjugate prepared in step (a') and linking the other end of the non-peptidyl polymer of the isolated conjugate to the other of the immunoglobulin Fc region and the physiologically active polypeptide by a covalent bond, in which the reaction mole ratio between the conjugate and the immunoglobulin Fc region or the physiologically active polypeptide is in the range from 1:0.1 to 1:20, a reducing agent is contained in the range from 1 mM to 100 mM, and the reaction is performed in the condition of pH from 4.0 to 9.0, at a temperature from 4.0° C. to 25° C., and the reaction concentration of the immunoglobulin Fc region or physiologically active polypeptide is in the range from 0.1 mg/mL to 100 mg/mL; and (c') isolating the protein complex, essentially comprising the covalently linked physiologically active polypeptide, non-peptidyl polymer, and immunoglobulin Fc region prepared in step (b'), in which the non-peptidyl polymer is linked to the N-terminus of the immunoglobulin Fc fragment.

Still another specific embodiment of the present invention provides a method for preparing the protein complex with N-terminal selectivity of 90% or higher.

Still another aspect of the present invention provides a pharmaceutical composition for improving in vivo duration and stability of the physiologically active polypeptide comprising the protein complex as an active ingredient.

A specific embodiment of the present invention provides a composition comprising the protein complex in an amount of 90% or higher.

Still another aspect of the present invention is a pharmaceutical container containing the preparation for delivery of the present composition. Exemplary pharmaceutical containers include an injector, a syringe, vial, infusion bottle, ampoule or carpoule, for example, a syringe equipped with a needle protection system or a carpoule within an injection pen. According to one embodiment, the present invention provides an injector that includes a container having a wall with an interior surface and a seal assembly with an interior surface, the interior surfaces of the wall and the seal assembly defining a closed sterile reservoir filled with a drug product.

The injector may also include a fluid delivery system comprising a clean, unsheathed, rigid container needle having a point disposed only partially through the seal assembly in a storage state, and disposed through the interior surface of the seal assembly into the sterile reservoir in a delivery state. Further, the injection may include an actuator that is adapted to move the container needle from the storage state to the delivery state. In one embodiment, the wall of the container may be a rigid wall or a flexible wall, and the seal assembly may be a flexible unitary wall having an interior surface that defines the interior surface of the seal assembly. The flexible unitary wall may define a septum disposed across the opening and fixedly attached to the wall of the container. Alternatively, the wall of the container may define a bore, and the unitary flexible wall may define a stopper that is moveable along the bore. In such a case, the wall of the container may define a closed end opposite the stopper and an open end in which the stopper is disposed. As a further alternative, the wall of the container may define a bore with an opening in fluid communication with a first end of the bore, and the unitary flexible wall defines a septum disposed across the opening and fixedly attached to the wall of the container, the container further comprising a stopper that is disposed within a second end of the bore and is moveable along the bore.

Still another aspect of the present invention is directed to methods of treating, improving, or preventing neurological disorders in patients in need thereof. Such neurological disorders can be associated with chronic spinal cord injuries, Parkinson's disease, or neurodevelopmental disabilities such as cerebral palsy. The method comprises administering therapeutically effective doses to patients in need in connection to the neurological disorder and management thereof.

Still another aspect of the present invention provides for the use of the instant composition as set forth above in treatment relating to bone marrow transplantation. The method comprises administering therapeutically effective doses to patients in need in connection with bone marrow transplantation and mobilization of stem cells.

Definitions

As used herein, the term "protein complex" or "complex" refers to a structure in which at least one physiologically active polypeptide, at least one non-peptidyl polymer having a reactive group at both ends thereof, and at least one immunoglobulin Fc region are linked to each other via a covalent bond. Further, a structure in which only two molecules selected from the physiologically active polypeptide, the non-peptidyl polymer, and the immunoglobulin Fc region are linked to each other via a covalent bond is called "conjugate" in order to distinguish it from the "complex."

The protein complex of the present invention may be a protein complex in which the PEG is linked to the modified G-CSF and the immunoglobulin Fc region through reactive groups at both ends thereof by a covalent bond, respectively.

As used herein, the term "physiologically active polypeptide," "physiologically active protein," "active protein," or "protein drug" refers to a polypeptide or a protein having some kind of antagonistic activity to a physiological event in vivo, and these terms may be used interchangeably.

As used herein, the term "non-peptidyl polymer" refers to a biocompatible polymer including two or more repeating units which are linked to each other by any covalent bond excluding a peptide bond, but is not limited thereto.

As used herein, the term "immunoglobulin Fc region" refers to a region of an immunoglobulin molecule, except for the variable regions of the heavy and light chains, the heavy-chain constant region 1 (CH1) and the light chain constant region 1 (CL1) of an immunoglobulin. The immunoglobulin Fc region may further include a hinge region at the heavy-chain constant region. In particular, the immunoglobulin Fc region of the present invention may be a fragment including a part or all of the Fc region, and in the present invention, the immunoglobulin Fc region may be used interchangeably with an immunoglobulin fragment.

A native Fc has a sugar chain at position Asn297 of heavy-chain constant region 1, but *E. coli*-derived recombinant Fc is expressed as an aglycosylated form. The removal of sugar chains from Fc results in a decrease in binding affinity of Fc gamma receptors 1, 2, and 3 and complement (clq) to heavy-chain constant region 1, leading to a decrease or loss in antibody-dependent cell-mediated cytotoxicity or complement-dependent cytotoxicity.

As used herein, the term "immunoglobulin constant region" may refer to an Fc fragment including heavy-chain constant region 2 (CH2) and heavy-chain constant region 3 (CH3) (or containing heavy-chain constant region 4 (CH4)), except for the variable regions of the heavy and light chains, the heavy-chain constant region 1 (CHI) and the light chain constant region (CL) of an immunoglobulin, and may further include a hinge region at the heavy chain constant region. Further, the immunoglobulin constant region of the present invention may be an extended immunoglobulin constant region including a part or all of the Fc region including the heavy-chain constant region 1 (CH1) and/or the light chain constant region (CL), except for the variable regions of the heavy and light chains of an immunoglobulin, as long as it has a physiological function substantially similar to or better than the native protein.

Meanwhile, the immunoglobulin constant region may originate from humans or animals, such as cows, goats, pigs, mice, rabbits, hamsters, rats, guinea pigs, etc., and may preferably be of human origin. In addition, the immunoglobulin constant region may be selected from constant regions derived from IgG, IgA, IgD, IgE, IgM, or combinations or hybrids thereof, preferably, derived from IgG or IgM, which are the most abundant thereof in human blood, and most preferably, derived from IgG, which is known to improve the half-life of ligand-binding proteins. In the present invention, the immunoglobulin Fc region may be a dimer or multimer consisting of single-chain immunoglobulins of domains of the same origin.

As used herein, the term "combination" means that polypeptides encoding single-chain immunoglobulin constant regions (preferably Fc regions) of the same origin are linked to a single-chain polypeptide of a different origin to form a dimer or multimer. That is, a dimer or a multimer may be prepared from two or more fragments selected from the group consisting of Fc fragments of IgG Fc, IgA Fc, IgM Fc, IgD Fc, and IgE Fc.

As used herein, the term "hybrid" means that sequences encoding two or more immunoglobulin constant regions of different origins are present in a single-chain of an immunoglobulin constant region (preferably, an Fc region). In the present invention, various hybrid forms are possible. For example, the hybrid domain may be composed of one to four domains selected from the group consisting of CH1, CH2, CH3, and CH4 of IgG Fc, IgM Fc, IgA Fc, IgE Fc, and IgD Fc, and may further include a hinge region.

IgG may be divided into the IgG1, IgG2, IgG3, and IgG4 subclasses, and the present invention may include combinations or hybrids thereof. Preferred are the IgG2 and IgG4 subclasses, and most preferred is the Fc region of IgG4 rarely having effector functions such as complement dependent cytotoxicity (CDC).

The immunoglobulin constant region may have the glycosylated form to the same extent as, or to a greater or lesser extent than the native form or may be the deglycosylated form. Increased or decreased glycosylation or deglycosylation of the immunoglobulin constant region may be achieved by typical methods, for example, by using a chemical method, an enzymatic method or a genetic engineering method using microorganisms. Herein, when deglycosylated, the complement (Clq) binding to an immunoglobulin constant region becomes significantly decreased, and antibody-dependent cytotoxicity or complement-dependent cytotoxicity is reduced or removed, thereby not inducing unnecessary immune responses in vivo. In this context, deglycosylated or aglycosylated immunoglobulin constant regions are more consistent with the purpose of drug carriers. Accordingly, the immunoglobulin Fc region may be more specifically an aglycosylated Fc region derived from human IgG4, that is, a human IgG4-derived aglycosylated Fc region. The human-derived Fc region is more preferable than a non-human derived Fc region, which may act as an antigen in the human body and cause undesirable immune responses such as the production of a new antibody against the antigen.

Further, the immunoglobulin constant region of the present invention includes not only the native amino acid sequence but also sequence derivatives (mutants) thereof. The amino acid sequence derivative means that it has an amino acid sequence different from the wild-type amino acid sequence as a result of deletion, insertion, conserved or non-conserved substitution of one or more amino acid residues, or a combination thereof. For instance, amino acid residues at positions 214 to 238, 297 to 299, 318 to 322, or 327 to 331 in IgG Fc, known to be important for linkage, may be used as the sites suitable for modification. Various derivatives, such as those prepared by removing the sites capable of forming disulfide bonds, removing several N-terminal amino acids from native Fc, or adding methionine to the N-terminus of native Fc, may be used. In addition, complement fixation sites, e.g., Clq fixation sites, or ADCC sites, may be eliminated to remove the effector function. The techniques of preparing the sequence derivatives of the immunoglobulin constant region are disclosed in International Patent Publication Nos. WO 97/34631 and WO 96/32478.

Amino acid substitutions in a protein or peptide molecule that do not alter the activity of the molecule are well known in the art (H. Neurath, R. L. Hill, The Proteins, Academic Press, New York, 1979). The most common substitutions occur between amino acid residues Ala/Ser, Val/Ile, Asp/Glu, Thr/Ser, AlaJGly, Ala/Thr, Ser/Asn, Ala/Val, Ser/Gly, Thr/Phe, Ala/Pro, Lys/Arg, Asp/Asn, Leu/Ile, LeuNal, Ala/Glu, and Asp/Gly, in both directions. Optionally, amino acids may be modified by phosphorylation, sulfation, acrylation, glycosylation, methylation, farnesylation, acetylation, amidation, or the like.

The above-described immunoglobulin constant region derivative may be a derivative which has a biological activity equivalent to that of the immunoglobulin constant region of the present invention, but has increased structural stability of the immunoglobulin constant region against heat, pH, etc. Further, the immunoglobulin constant region may be obtained from a native type isolated from humans or animals such as cows, goats, pigs, mice, rabbits, hamsters, rats, guinea pigs, etc., or may be their recombinants or derivatives obtained from transformed animal cells or microorganisms. Herein, they may be obtained from a native immunoglobulin by isolating whole immunoglobulins from human or animal organisms and treating them with a proteolytic enzyme. Papain digests the native immunoglobulin into Fab and Fc regions, and pepsin treatment results in the production of pF'c and F(ab)2 fragments. These fragments may be subjected, for example, to size exclusion chromatography to isolate Fc or pF'c.

Preferably, a human-derived immunoglobulin constant region may be a recombinant immunoglobulin constant region that is obtained from a microorganism.

The protein complex of the present invention may include one or more of a unit structure of a [physiologically active polypeptide/non-peptidyl polymer/immunoglobulin Fc region], in which all components may be linked in a linear form by a covalent bond. The non-peptidyl polymer may have a reactive group at both ends thereof and is linked to the physiologically active polypeptide and the immunoglobulin Fc region through the reactive group by a covalent bond, respectively. That is, at least one conjugate of the physiologically active polypeptide and the non-peptidyl polymer is linked to one immunoglobulin Fc region by a covalent bond, thereby forming a monomer, dimer, or multimer of the physiologically active polypeptide, which is mediated by the immunoglobulin Fc region. Therefore, an increase in vivo activity and stability may be more effectively achieved.

The reactive group at both ends of the non-peptidyl polymer is preferably selected from the group consisting of a reactive aldehyde group, a propionaldehyde group, a butyraldehyde group, a maleimide group, and a succinimide derivative. The succinimide derivative may be hydroxy succinimidyl, succinimidyl carboxymethyl, succinimidyl valerate, succinimidyl methyl butanoate, succinimidyl methyl propionate, succinimidyl butanoate, succinimidyl propionate, N-hydroxysuccinimide, or succinimidyl carbonate. In particular, when the non-peptidyl polymer has a reactive aldehyde group at both ends, it is effective in linking both of the ends with the physiologically active polypeptide and the immunoglobulin with minimal non-specific reactions. A final product generated by reductive alkylation by an aldehyde bond is much more stable than when linked by an amide bond.

The reactive groups at both ends of the non-peptidyl polymer of the present invention may be the same as or different from each other. The non-peptide polymer may possess aldehyde reactive groups at both ends, or it may possess an aldehyde group at one end and a maleimide reactive group at the other end, or an aldehyde group at one end and a succinimide reactive group at the other end, but is not limited thereto.

For example, the non-peptide polymer may possess a maleimide group at one end and an aldehyde group, a propionaldehyde group, or a butyraldehyde group at the other end. Also, the non-peptide polymer may possess a succinimidyl group at one end and a propionaldehyde group, or a butyraldehyde group at the other end. When a polyethylene glycol having a reactive hydroxy group at both ends thereof is used as the non-peptidyl polymer, the hydroxy group may be activated to various reactive groups by known chemical reactions, or a commercially available polyethylene glycol having a modified reactive group may be used so as to prepare the protein complex of the present invention.

When the physiologically active polypeptide and the immunoglobulin Fc region are linked via the non-peptidyl polymer, each of both of the ends of the non-peptidyl polymer may bind to the N-terminus of the immunoglobulin Fc region and the N-terminus (amino terminus), C-terminus (carboxy terminus), or free reactive group of a lysine residue, a histidine residue, or a cysteine residue of the physiologically active polypeptide.

As used herein, the term "N-terminus" refers to an N-terminus of a peptide, which is a site to which a linker including a non-peptidyl polymer can be conjugated for the purpose of the present invention. Examples of the N-terminus may include not only amino acid residues at the distal end of the N-terminus, but but also amino acid residues near the N-terminus, but are not limited thereto. Specifically, the 1st to the 20th amino acid residues from the distal end may be included.

The non-peptidyl polymer of the present invention may be selected from the group consisting of polyethylene glycol, polypropylene glycol, copolymers of ethylene glycol and propylene glycol, polyoxyethylated polyols, polyvinyl alcohol, polysaccharides, dextran, polyvinyl ethyl ether, biodegradable polymers such as PLA (polylactic acid) and PLGA (polylactic-glycolic acid), lipid polymers, chitins, hyaluronic acid, and combinations thereof, and specifically, polyethylene glycol, but is not limited thereto. Also, derivatives thereof well known in the art and easily prepared within the skill of the art are included in the non-peptidyl polymer of the present invention. The non-peptidyl polymer may have a molecular weight in the range of 1 kDa to 100 kDa, and specifically 1 kDa to 20 kDa.

The physiologically active polypeptide of the present invention may be exemplified by various physiologically active polypeptides such as hormones, cytokines, interleukins, interleukin-binding proteins, enzymes, antibodies, growth factors, transcription factors, blood factors, vaccines, structural proteins, ligand proteins or receptors, cell surface antigens, receptor antagonists, and derivatives or analogs thereof.

Specifically, the physiologically active polypeptide includes human growth hormones, growth hormone-releasing hormones, growth hormone-releasing peptides, interferons and interferon receptors (e.g., interferon-alpha, -beta, and -gamma, soluble type I interferon receptors), colony-stimulating factors, interleukins (e.g., interleukin-1, -2, -3, -4, -6, -7, -8, -9, -10, -11, -12, -13, -14, -15, -16, -17, -18, -19, -20, -21, -22, -23, -24, -25, -26, -27, -28, -29. -30. Etc.), and interleukin receptors (e.g; IL-1 receptor. IL-4 receptor, etc.), enzymes (e.g., glucocerebrosidase, iduronate-2-sulfatase, alpha-galactosidase-A, agalsidase alpha,beta, alpha-L-iduronidase, butyrylcholinesterase, chitinase, glutamate decarboxylase, imiglucerase, lipase, uricase, platelet-activating factor acetylhydrolase, neutral endopeptidase, myeloperoxidase, etc.), interleukin- and cytokine-binding proteins (e.g., IL-18 bp, TNF-binding protein, etc.), macrophage-activating factors, macrophage peptides, B-cell factors, T-cell factors, protein A, allergy inhibitors, cell necrosis glycoproteins, immunotoxins, lymphotoxins, tumor necrosis factor, tumor suppressors, transforming growth factor, alpha-1 anti-trypsin, albumin, alpha-lactalbumin, apolipoprotein-E, erythropoietin, glycosylated crythropoictin, angiopoietins, hemoglobin, thrombin, thrombin receptors activating peptides, throm-bomodulin, blood factors VII, VIIa, VIII, IX, and XIII, plasminogen activators, fibrin-binding peptides, urokinase, streptokinase, hirudin, protein C, C-reactive protein, renin inhibitor, collagenase inhibitor, superoxide dismutase, leptin, platelet-derived growth factor, epithelial growth factor, epidermal growth factor, angiostatin, angiotensin, bone growth factor, bone-stimulating protein, calcitonin, insulin, oxyntomodulin, glucagon, glucagon derivatives, glucagon-like peptides, exendins (Exendin4), atriopeptin, cartilage-inducing factor, elcatonin, connective tissue-activating factor, tissue factor pathway inhibitor, follicle-stimulating hormone, luteinizing hormone, luteinizing hormone-releasing hormone, nerve growth factors (e.g., nerve growth factor, cilliary neurotrophic factor, axogenesis factor-1, brain-natriuretic peptide, glial-derived neu-ro-trophic factor, netrin, neutrophil inhibitor factor, neurotrophic factor, neurturin, etc.), parathyroid hormone, relaxin, secretin, somatomedin, insulin-like growth factor, adrenocortical hormone, glucagon, cholecystokinin, pancreatic polypeptide, gastrin-releasing peptide, corticotrophin-releasing factor, thyroid-stimulating hormone, autotaxin, lactoferrin, myostatin, receptors (e.g., TNFR (P75), TNFR (P55), IL-1 receptor, VEGF receptor, B-cell-activating factor receptor, etc.), receptor antagonists (e.g., IL1-Ra, etc.), cell surface antigens (e.g., CD 2, 3, 4, 5, 7, 11a, 11b, 18, 19, 20, 23, 25, 33, 38, 40, 45, 69, etc.), monoclonal antibodies, polyclonal antibodies, antibody fragments (e.g., scFv, Fab, Fab', F(ab')2, and Fd), and virus-derived vaccine antigens.

Specifically, the physiologically active polypeptide of the present invention may be granulocyte colony-stimulating factor, erythropoietin, or modified versions thereof. In the preferred embodiment, the polypeptide is G-CSF.

In the present invention, the antibody fragment may be Fab, Fab', F(ab'), Fd, or scFv having an ability to bind to a specific antigen, and preferably, Fab.' The Fab fragments include the variable domain (VL) and constant domain (CL)

of the light chain and the variable domain (VH) and the first constant domain (CH1) of the heavy chain. The Fab' fragments differ from the Fab fragments in terms of the addition of several amino acid residues including one or more cysteine residues from the hinge region at the carboxyl terminus of the CH1 domain. The Fd fragments are fragments consisting of only the VH and CH1 domains, and the F(ab')2 fragments are produced by binding of two molecules of Fab' fragments by either disulfide bonding or a chemical reaction. The scFv fragment is a single polypeptide chain, in which only VL and VH domains are linked to each other by a peptide linker Further, the protein complex of the present invention may be used in the development of long-acting protein formulations of animal growth hormone such as bovine growth hormone or porcine growth hormone, and long-acting protein formulations for treatment or prevention of animal disease, such as interferon.

Another aspect of the present invention provides a method of preparing the protein complex of the present invention. In particular, the present invention provides a method of preparing a position-specific protein complex, the method comprising: (a) preparing a protein complex by linking at least one non-peptidyl polymer having a reactive group at both ends, at least one physiologically active polypeptide, and at least one immunoglobulin Fc region by a covalent bond, and (b) isolating the protein complex, essentially including the covalently linked physiologically active polypeptide, non-peptidyl polymer, and immunoglobulin Fc region prepared in step (a), in which the non-peptidyl polymer is linked to the N-terminus of the immunoglobulin Fc fragment.

The immunoglobulin Fc region of the present invention may be in the form of a dimer, or in the form of a homodimer or heterodimer. Therefore, the immunoglobulin Fc region constituting the protein complex of the present invention may include one or two or more of an N-terminus. Thus, the immunoglobulin Fc region may be linked to at least one non-peptidyl polymer via the N-terminus. In particular, the immunoglobulin Fc region of the present invention may be in the form of a homodimer, and therefore, linked to one or two non-peptidyl polymers via two N-terminals included in the homodimer of the immunoglobulin Fc region. In this regard, the non-peptidyl polymers may bind to the physiologically active polypeptides, respectively, thereby forming the protein complex.

Accordingly, the protein complex of the present invention may be prepared by linking one or two or more of the non-peptidyl polymer, one or two or more of the physiologically active polypeptide, and one or two or more of the immunoglobulin Fc region via a covalent bond.

In step (a), the covalent bonds between the three components may occur sequentially or at the same time. For example, when the physiologically active polypeptide and the immunoglobulin Fc region are linked to both ends of the non-peptidyl polymer, respectively, any one of the physiologically active polypeptide and the immunoglobulin Fc region may be first linked to one end of the non-peptidyl polymer, and then the other may be linked to the other end of the non-peptidyl polymer. This method is advantageous in that production of by-products other than the desired protein complex is minimized, and the protein complex is prepared in high purity.

Therefore, step (a) may comprise:

(i) linking a specific site of the immunoglobulin Fc region or the physiologically active polypeptide to one end of the non-peptidyl polymer via a covalent bond;

(ii) homogeneously isolating a conjugate from the reaction mixture, in which the conjugate is prepared by linking the specific site of the immunoglobulin Fc region or the physiologically active polypeptide to the non-peptidyl polymer; and (iii) producing a protein complex by linking the physiologically active polypeptide or the specific site of the immunoglobulin Fc region to the other end of the non-peptidyl polymer of the isolated conjugate.

Meanwhile, in the present invention, step (a) includes (a1) preparing a conjugate by linking one end of the non-peptidyl polymer to any one of the immunoglobulin Fc region and the physiologically active polypeptide by a covalent bond; and (a2) isolating the conjugate prepared in step (a1) and linking the other end of the non-peptidyl polymer of the isolated conjugate to the other of the physiologically active polypeptide and the immunoglobulin Fc region by a covalent bond.

Specifically, step (a) may comprise (a1') preparing a conjugate by linking one end of the non-peptidyl polymer to the immunoglobulin Fc region by a covalent bond; and (a2') isolating the conjugate prepared in step (a1') and linking the other end of the non-peptidyl polymer of the isolated conjugate to the physiologically active polypeptide by a covalent bond.

Alternatively, step (a) may include (a1") preparing a conjugate by linking one end of the non-peptidyl polymer to the physiologically active polypeptide by a covalent bond; and (a2") isolating the conjugate prepared in step (a1") and linking the other end of the non-peptidyl polymer of the isolated conjugate to the immunoglobulin Fc region by a covalent bond.

In step (a1), (a1'), or (a1") of the present invention, the reaction mole ratio between the physiologically active polypeptide and the non-peptidyl polymer may be in the range from 1:1 to 1:30, and the reaction mole ratio between the immunoglobulin Fc region and the non-peptidyl polymer may be in the range from 1:1 to 1:20.

Specifically, in step (a1'), the reaction mole ratio between the immunoglobulin Fc region and the non-peptidyl polymer may be in the range from 1:1 to 1:20, and in particular, in the range from 1:1 to 1:15, 1:1 to 1:10, or 1:1 to 1:4. In step (a1"), the reaction mole ratio between the physiologically active polypeptide and the non-peptidyl polymer may be in the range from 1:1 to 1:30, and in particular, in the range from 1:1 to 1:15 or 1:1 to 1:10. A preparation yield and cost may be optimized depending on the reaction mole ratio.

In the present invention, step (a1), (a1'), or (a1") may be performed in a pH condition from 4.0 to 9.0; step (a1), (a1'), or (a1") may be performed at a temperature from 4.0° C. to 25° C.; in step (a1), (a1'), or (a1"), the reaction concentration of the immunoglobulin Fc region or physiologically active polypeptide may be in the range from 0.1 mg/mL to 100 mg/mL.

In step (a2), (a2'), or (a2") of the present invention, the reaction mole ratio between the conjugate and the immunoglobulin Fc region or the physiologically active polypeptide may be in the range from 1:0.1 to 1:20, and in particular, in the range from 1:0.2 to 1:10. Specifically, in step (a2'), the reaction mole ratio between the conjugate and the physiologically active polypeptide may be in the range from 1:0.1 to 1:20, and in step (a2"), the reaction mole ratio between the conjugate and the immunoglobulin Fc region may be in the range from 1:0.1 to 1:20. A preparation yield and cost may be optimized depending on the reaction mole ratio.

In the present invention, step (a2), (a2'), or (a2") may be performed in a pH condition from 4.0 to 9.0; step (a2), (a2'), or (a2″) may be performed at a temperature from 4.0° C. to 25° C.; in step (a2), (a2'), or (a2″), the reaction concentration of the immunoglobulin Fc region or physiologically active polypeptide may be in the range from 0.1 mg/mL to 100 mg/mL.

Meanwhile, the preparation method of the present invention may be a method of preparing a position-specific protein complex, including (a') preparing a conjugate by linking one end of the non-peptidyl polymer to any one of the immunoglobulin Fc region and the physiologically active polypeptide by a covalent bond, in which the reaction mole ratio between the physiologically active polypeptide and the non-peptidyl polymer is in the range from 1:1 to 1:30, the reaction mole ratio between the immunoglobulin Fc region and the non-peptidyl polymer is in the range from 1:1 to 1:20, a reducing agent is contained in the range from 1 mM to 100 mM, the reaction is performed in the condition of pH from 4.0 to 9.0, at a temperature from 4.0° C. to 25° C., and the reaction concentration of the immunoglobulin Fc region or physiologically active polypeptide is in the range from 0.1 mg/mL to 100 mg/mL;

(b') isolating the conjugate prepared in step (a') and linking the other end of the non-peptidyl polymer of the isolated conjugate to the other of the immunoglobulin Fc region and the physiologically active polypeptide by a covalent bond, in which the reaction mole ratio between the conjugate and the immunoglobulin Fc region or the physiologically active polypeptide is in the range from 1:0.1 to 1:20, a reducing agent is contained in the range from 1 mM to 100 mM, the reaction is performed in the condition of pH from 4.0 to 9.0, at a temperature from 0° C. to 25° C., and the concentration of the immunoglobulin Fc region or physiologically active polypeptide is in the range from 0.1 mg/mL to 100 mg/mL; and (c') isolating the protein complex, essentially including the covalently linked physiologically active polypeptide, non-peptidyl polymer, and immunoglobulin Fc region prepared in step (b'), in which the non-peptidyl polymer is linked to the N-terminus of the immunoglobulin Fc fragment, but is not limited thereto.

The reactions in step (a1), step (a1'), step (a1″), step (a2), step (a2'), and step (a2″) of the present invention may be performed in the presence of a reducing agent, considering the type of the reactive groups at both ends of the non-peptidyl polymer which participate in the reactions, if necessary. The reducing agent of the present invention may be sodium cyanoborohydride (NaCNBH3), sodium borohydride, dimethylamine borate, or pyridine borate. In this regard, a concentration of the reducing agent (e.g., sodium cyanoborohydride), temperature and pH of a reaction solution, and total concentrations of the physiologically active polypeptide and the immunoglobulin Fc region participating in the reaction are important in terms of production yield and purity. To maximize the production of a high-purity homogeneous complex, various combinations of the conditions are needed. According to the feature of the physiologically active polypeptide to be prepared, various conditions are possible, but not limited to, the reducing agent (e.g., sodium cyanoborohydride) may be contained in the range from 1 mM to 100 mM, the reaction solution may be at a temperature from 0° C. to 25° C. and in the condition of pH from 4.0 to 9.0, and the concentration of the reaction protein (concentration of the immunoglobulin Fc region or physiologically active polypeptide included upon the reaction) may be in the range from 5 mg/mL to 100 mg/mL.

Meanwhile, the separation of the conjugate in step (a2), step (a2'), and step (a2″) may be performed, if necessary, by a method selected from general methods which are used in protein separation, considering the properties such as purity, hydrophobicity, molecular weight, and electrical charge which are required for the separated conjugate. For example, the separation may be performed by applying various known methods, including size exclusion chromatography, affinity chromatography, hydrophobic chromatography, or ion exchange chromatography, and if necessary, a plurality of different methods are used in combination to purify the conjugate with higher purity.

According to the features of the physiologically active polypeptide to be prepared, various conditions are possible. However, in order to separate the immunoglobulin Fc region or the physiologically active polypeptide conjugate linked to the non-peptidyl polymer, size exclusion chromatography is generally performed. For further scale-up and separation of isomers generated by binding of the non-peptidyl polymer at a position other than the desired position or a small amount of denatured forms generated during preparation, affinity chromatography, hydrophobic chromatography, or ion exchange chromatography may also be used.

In the present invention, step (b) may be performed, if necessary, by a method selected from general methods which are used in protein separation, considering the properties such as hydrophobicity, molecular weight, and electrical charge, in order to finally purify a high-purity complex. For example, the separation may be performed by applying various known methods, including size exclusion chromatography, affinity chromatography, hydrophobic chromatography, or ion exchange chromatography, and if necessary, a plurality of different methods are used in combination to purify the complex with higher purity. According to the features of the desired complex consisting of the physiologically active polypeptide, the non-peptidyl polymer, and the Fc constant region, various separation conditions are possible. However, in order to separate the complex in which the physiologically active polypeptide and the immunoglobulin Fc region are respectively linked to both ends of the non-peptidyl polymer, size exclusion chromatography is generally performed. For further scale-up and effective separation of isomers or side-reaction products generated by binding of the physiologically active polypeptide or the immunoglobulin Fc region, and non-peptidyl polymer at a position other than the desired position, or a small amount of denatured forms generated during preparation, unreacted physiologically active polypeptide, non-peptidyl polymer, and immunoglobulin Fc region, hydrophobic chromatography, ion exchange chromatography, or affinity chromatography may be used in combination. In particular, hydrophobic chromatography and ion exchange chromatography may be used in combination, and a plurality of hydrophobic chromatography or a plurality of ion exchange chromatography is also possible. According to the complex to be prepared, ion exchange chromatography or hydrophobic chromatography may be used singly.

In the present invention, the ion exchange chromatography is to separate a protein by passing charged protein at a specific pH through a charged ion resin-immobilized chromatography column and separating the protein by a difference in the migration rate of the protein, and it may be anion exchange chromatography or cation exchange chromatography.

The anion exchange chromatography is to use a cation resin, and a functional group of the resin constituting the corresponding anion exchange chromatography may be any one selected from the group consisting of quaternary ammonium (Q), quaternary aminoethyl (QAE), diethylaminoethyl (DEAE), polyethylene amine (PEI), dimethyl-aminomethyl (DMAE), and trimethylaminoethyl (TMAE), but is not limited thereto.

Further, the cation exchange chromatography is to use an anion resin, and a functional group of the resin constituting the corresponding cation exchange chromatography may be any one selected from the group consisting of methylsulfonate (S), sulfopropyl (SP), carboxymethyl (CM), sulfoethyl (SE), and polyaspartic acid, but is not limited thereto.

In the present invention, a functional group of the resin constituting the hydrophobic chromatography may be any one selected from the group consisting of phenyl, octyl, (iso)propyl, butyl, and ethyl, but is not limited thereto.

In the present invention, a functional group of the resin constituting the size exclusion chromatography may be any one selected from the group consisting of Superdex, Sephacryl, Superpose, and Sephadex, but is not limited thereto.

Furthermore, the affinity chromatography in the present invention is to separate a protein by a difference in the migration rate of the protein, which is caused by the interaction between the protein and a ligand capable of interacting with the protein in a resin onto which the ligand is immobilized. A functional group of the resin constituting the affinity chromatography may be any one selected from the group consisting of protein A, heparin, blue, benzamidine, metal ions (cobalt, nickel, and copper), and an antibody to a part or the entirety of the constituting components of the protein complex, in which both ends of the non-peptidyl polymer are respectively conjugated to the immunoglobulin Fc region and the physiologically active polypeptide, but is not limited thereto.

In the present invention, step (b) is to isolate the protein complex in which the non-peptidyl polymer and the immunoglobulin Fc region are linked to each other via the N-terminus of the immunoglobulin Fc region.

Still another aspect of the present invention provides a method for preparing a protein complex with N-terminal selectivity of 90% or higher. Specifically, the protein complex prepared by the method of the present invention may be one, in which one end of the non-peptidyl polymer may be linked to the N-terminus of the immunoglobulin Fc region with N-terminal selectivity of 90% or higher, more specifically 95% or higher, even more specifically 98% or higher, and yet even more specifically 99% or higher, but is not limited thereto.

As used herein, the term "linking with N-terminal selectivity of 90% or higher" means that, in 90% or more of the protein complex prepared by purification of the protein complex fractions obtained by a series of reactions according to the present invention, the non-peptidyl polymer is linked to the N-terminus of the Fc region in a position-specific manner. As used herein, the term "90% or higher" may refer to v/v, w/w, and peak/peak, but is not limited to a particular unit. The yield of the protein complex comprising the non-peptidyl polymer linked to the N-terminus of the Fc region in a position-specific manner may vary by reaction conditions, a reactor of the non-peptidyl polymer, etc.

In Examples of the present invention, it was confirmed that a protein complex with N-terminal selectivity of 90% or higher can be prepared by the method according to the present invention, via preparation of various physiologically active polypeptides, non-peptidyl polymers, and Fc complexes.

The pharmaceutical composition may comprise a protein complex, which includes the physiologically active polypeptide-non-peptidyl polymer-N-terminus of an immunoglobulin Fc region, in an amount of 90% or higher, more specifically 95% or higher, even more specifically 98% or higher, and yet even more specifically 99% or higher, but is not limited thereto. As used herein, the term "90% or higher" may refer to v/v, w/w, and peak/peak, but is not limited to a particular unit.

The pharmaceutical composition may further include a pharmaceutically acceptable excipient.

The pharmaceutical composition of the present invention may be administered via various routes including oral, percutaneous, subcutaneous, intravenous, and intramuscular routes, preferably, in the form of an injectable formulation. Further, the pharmaceutical composition of the present invention may be formulated by a method known in the art in order to provide rapid, long-lasting, or delayed release of the active ingredient after administration thereof to a mammal. The formulation may be a tablet, a pill, a powder, a sachet, an elixir, a suspension, an emulsion, a solution, a syrup, an aerosol, a soft or hard gelatin capsule, a sterile injectable solution, or a sterile powder. Examples of suitable carriers, excipients, and diluents may include lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinyl pyrrolidone, water, methyl hydroxybenzoate, propyl hydroxybenzoate, talc, magnesium stearate, and mineral oil. The pharmaceutical composition may further include a filler, an anticoagulant, a lubricant, a wetting agent, a flavoring agent, an emulsifying agent, a preservative, etc.

A practical administration dose of the protein complex of the present invention may be determined by several related factors including the types of diseases to be treated, administration routes, the patient's age, gender, weight, and severity of the illness, as well as by the types of the physiologically active polypeptide as an active component. Since the protein complex of the present invention has excellent blood duration and in vivo potency, it can remarkably reduce the administration dose and frequency of a peptide drug, including the protein complex of the present invention.

Still another aspect of the present invention provides a population of protein complexes, including the protein complex prepared according to the above method in an amount of 90% or higher. As used herein, the terms "population of complex", and "population" may be used interchangeably, and they refer to a group of protein complexes including protein complexes, in which a non-peptidyl polymer is linked to the N-terminus of an Fc region, and/or protein complexes, in which a non-peptidyl polymer is linked to a region other than the N-terminus of an Fc region.

The population may include only the protein complexes, in which a non-peptidyl polymer is linked to the N-terminus of an Fc region, or the protein complexes, in which a non-peptidyl polymer is linked to a region other than the N-terminus of an Fc region. Specifically, the percentage of the protein complexes, in which a non-peptidyl polymer is linked to a region other than the N-terminus of an Fc region, included in the population may be 90% or higher, more specifically 95% or higher, even more specifically 98% or higher, and yet even more specifically 99% or higher, but is not limited thereto. As used herein, the term "90% or higher" may refer to v/v, w/w, and peak/peak, but is not limited to a particular unit.

For the purpose of the present invention, the population may refer to a population with an increased percentage of the protein complexes, in which a non-peptidyl polymer is linked to a region other than the N-terminus of an Fc region, by removing impurities, unreacted materials, etc., from the protein complexes prepared thereof. Additionally, the population may refer to one which was prepared by a method for preparing protein complexes with N-terminal selectivity of 90% or higher, but is not limited thereto. The population may be efficiently purified by the method of the present invention.

The present invention is particularly directed to the use of the above-described protein complexes in preventing, alleviating, or treating patient in need thereof having a need in increasing their white blood cell production, count, or are in need of increasing stem cell production by administering to the patient a therapeutically effective amount of a protein complex comprising a modified human granulocyte-colony stimulating factor (hG-CSF) covalently linked to an immunoglobulin Fc region via a non-peptidyl polymer, wherein the non-peptidyl polymer is site-specifically linked to an N-terminus of the immunoglobulin Fc region, and the modified hG-CSF comprises substitutions in at least one of Cys17 and Pro65. Such methodologies may or may not be in combination with chemotherapeutic agents or regimens including docetaxel, doxorubicin, cyclophosphamide (TAC); dose-dense doxorubicin plus cyclophosphamide (AC), with or without subsequent weekly or semiweekly paclitaxel; and docetaxel plus cyclophosphamide (TC). Regardless, the methodologies described in this invention provides superior clinical and side effect outcomes for patients receiving such a regimen. In preferred embodiments, EFLAPEGRASTIM is administered at 13.2 mg/0.6 mL (containing 3.6 mg G-CSF) fixed dose. In one embodiment, TC is administered on Day 1 of each cycle intravenously (IV). Accordingly, Docetaxel is administered at 75 mg/m$^2$ IV infusion and (ii) Cyclophosphamide is administered at 600 mg/m$^2$ IV infusion. Each treatment cycle is 21 days, with up to a maximum of 4 cycles of chemotherapy. To begin full-dose chemotherapy on Day 1 of any cycle (Day 22 of the previous cycle), patients must show ANC≥1.5×10$^9$/L and a platelet count≥100×10$^9$/L. In other embodiments, EFLAPEGRASTIM may be administered on Day 2 of each cycle, approximately 24 hours (±2 hours) after TC chemotherapy.

Examples provided here are for illustrative purposes only, and the invention is not intended to be limited by these Examples.

EXAMPLES

Example 1: Preparation of Complex of Interferon Alpha (IFNα)-PEG-N-Terminus Region of Immunoglobulin Fc 1-1. Preparation of IFNa-PEG Conjugate ALD-PEG-ALD (IDB, Korea), which is polyethylene glycol (PEG) having a molecular weight of 3.4 kDa and aldehyde reactive groups at both ends thereof, was added to 5 mg/mL of human interferon alpha-2b (hIFNa-2b, molecular weight: 19 kDa) dissolved in 100 mM phosphate buffer at a molar ratio of hIFNa:PEG of 1:5 to 1:10. A reducing agent, sodium cyanoborohydride (NaBH$_3$CN, Sigma) was added thereto at a final concentration of 20 mM and allowed to react at 4° C. to 8° C. under slow stirring for about 1 hour. To obtain a conjugate in which PEG is selectively linked to the amino terminus of interferon alpha and PEG and interferon alpha are linked to each other at a ratio of 1:1, the reaction mixture was subjected to SP HP (GE healthcare, USA) anion exchange chromatography to purify an IFNot-PEG conjugate with high purity.

1-2. Preparation of IFNa-PEG-Fc Complex

In order to link the IFNa-PEG conjugate purified in Example 1-1 to the N-terminal proline residue of immunoglobulin Fc, the immunoglobulin Fc fragment was added and reacted at a molar ratio of IFNa-PEG conjugate: immunoglobulin Fc of 1:1 to 1:4. The reaction solution was prepared as 100 mM phosphate buffer (pH 5.5 to 6.5), and sodium cyanoborohydride (NaBH$_3$CN, Sigma) was added as a reducing agent at a final concentration of 20 mM to 50 mM. The reaction was allowed at 4° C. to 8° C. for about 12 hours to 16 hours under slow stirring.

1-3. Isolation and Purification of IFNa-PEG-Fc Complex

In order to remove unreacted materials and by-products after the binding reaction of Example 1-2 and to purify the IFNa-PEG-Fc protein complex thus produced, the reaction mixture was buffer-exchanged to 10 mM Tris (pH 7.5), and then passed through a Source Q (GE healthcare, USA) anion exchange chromatography column to remove unreacted Fc and to obtain an IFNa-PEG-Fc protein complex fraction. In detail, the reaction solution was applied to Source Q column equilibrated with 10 mM Tris (pH 7.5), and the column was subjected to isocratic solvent washing using 20 mM Tris (pH 7.5) buffer solution containing 50 mM sodium chloride (NaCl) to remove impurities. Then, the IFNa-PEG-Fc protein complex was eluted with a concentration gradient of a buffer solution containing 150 mM sodium chloride (NaCl). A small amount of unreacted Fc and interferon alpha dimer were present as impurities in the obtained 1FNa-PEG-Fc protein complex fraction. In order to remove the impurities, Source iso (GE healthcare, USA) hydrophobic chromatography was further performed. In detail, Source iso (GE healthcare, USA) was equilibrated with a 20 mM potassium phosphate (pH 6.0) buffer solution containing about 1.3 M ammonium sulfate, and then the purified IFNa-PEG-Fc protein complex fraction was applied thereto. Finally, a high-purity IFNa-PEG-Fc protein complex was purified with a linear concentration gradient of a 20 mM potassium phosphate (pH 6.0) buffer solution. N-terminal selectivity of the Fc region of the prepared IFNa-PEG-Fc protein complex was examined by peptide mapping, and the selectivity was found to be 90% or higher.

Example 2: Preparation of Human Granulocyte Colony Stimulating Factor (G-CSF)-PEG-Fc Complex The $^{17,65S}$G-CSF-PEG-Fc protein complex was prepared using a derivative ($^{17,65}$-G-CSF) prepared by substituting serine for the amino acids at positions 17 and 65 of the native G-CSF and then purified.

2-1. Preparation of $^{17,65S}$G-CSF-PEG Conjugate

ALD-PEG-ALD (IDB, Korea), which is polyethylene glycol (PEG) having a molecular weight of 3.4 kDa and aldehyde reactive groups at both ends thereof, was added to 5 mg/mL of $^{17,65}$S-G-CSF (molecular weight: 18 kDa) dissolved in 100 mM phosphate buffer at a molar ratio of G-CSF:PEG of 1:5 to 1:10. A reducing agent, sodium cyanoborohydride (NaBH$_3$CN, Sigma), was added thereto at a final concentration of 20 mM and allowed to react at 4° C. to 8° C. under slow stirring for about 1 hour. To obtain a conjugate in which PEG is selectively linked to the amino terminus of human granulocyte colony stimulating factor and PEG and G-CSF are linked to each other at a ratio of 1:1, the reaction mixture was subjected to SP HP (GE healthcare, USA) cation exchange chromatography to purify a $^{17,65S}$G-CSF-PEG conjugate with a high purity.

2-2. Preparation of $^{17,65}$G-CSF-PEG-Fc Complex

In order to link the $^{17,65}$G-CSF-PEG conjugate purified in Example 3-1 to the N-terminus of immunoglobulin Fc, the immunoglobulin Fc fragment was added and reacted at a molar ratio of $^{17,65}$Ser-G-CSF-PEG conjugate: immunoglobulin Fc of 1:1 to 1:4. The reaction solution was prepared as a 100 mM phosphate buffer (pH 5.5 to 6.5), and sodium cyanoborohydride (NaCNBH3, Sigma) was added as a reducing agent at a final concentration of 20 mM. The reaction was allowed at 4° C. to 8° C. under slow stirring.

2-3. Isolation and Purification of $^{17,65}$Ser-G-CSF-PEG-Fc (or $^{17,65S}$G-CSF-PEG-Fc) Complex In order to remove unreacted materials and by-products after the binding reaction of Example 3-2 and to purify the $^{17,65S}$G-CSF-PEG-Fc protein complex thus produced, the reaction mixture was buffer-exchanged to 10 mM Tris (pH 8.0) containing 2 M NaCl and then passed through a Source Phenyl column. To remove impurities, the $^{17,65S}$G-CSF-PEG-Fc protein complex was purified with a concentration gradient of 20 mM Tris (pH 8.0) buffer solution. A small amount of unreacted immunoglobulin Fc and $^{17,65}$G-CSF dimer as impurities were present in the obtained $^{17,65S}$G-CSF-PEG-Fc protein complex fraction. In order to remove the impurities, Q HP (GE healthcare, USA) anion chromatography was further performed. Q HP (GE healthcare, USA) was equilibrated with a 20 mM Tris (pH 8.0) buffer solution, and then the purified $^{17,65S}$G-CSF-PEG-Fc protein complex fraction was applied thereto. Finally, a high-purity $^{17,65S}$ G-CSF-PEG-Fc protein complex was purified with a linear concentration gradient of a 20 mM Tris (pH 8.0) buffer solution containing 1 M sodium chloride. N-terminal selectivity of the Fc region of the prepared $^{17,65S}$G-CSF-PEG-Fc protein complex was examined by peptide mapping, and the selectivity was found to be 90% or higher.

Example 3: Preparation of Protein Complex Using PEG with Different Reactive Groups 3-1. Preparation of $^{17,65S}$G-CSF-PEG Conjugate SMB-PEG-SMB (Nektar, USA), which is polyethylene glycol (PEG) having a molecular weight of 3.4 kDa and succinimidyl alpha-methyl butanoate (SMB) reactive groups at both ends thereof, was added to 10 mg/mL of $^{17,65S}$G-CSF (molecular weight 18 kDa) dissolved in 20 mM phosphate buffer (pH 8.0) at a molar ratio of G-CSF:PEG of 1:3, and allowed to react at room temperature under slow stifling for about 30 minutes. To obtain a conjugate in which PEG is selectively linked to the amino terminus of $^{17,65S}$G-CSF and PEG and $^{17,65S}$G-CSF are linked to each other at a ratio of 1:1, the reaction mixture was subjected to SP HP (GE healthcare, USA) cation exchange chromatography.

3-2. Preparation of $^{17,65S}$G-CSF-PEG-Fc Complex

In order to link the $^{17,65S}$G-CSF-PEG conjugate purified in Example 7-1 to a region other than the N-terminus of immunoglobulin Fc, the immunoglobulin Fc fragment was added and reacted at a molar ratio of $^{17,65S}$G-CSF-PEG conjugate: immunoglobulin Fc of 1:4 to 1:8. The reaction was allowed in 20 mM phosphate buffer (pH 5.5 to 6.5) at room temperature for about 2 hours under slow stifling.

3-3. Isolation and Purification of $^{17,65S}$G-CSF-PEG-Fc Complex

In order to remove unreacted materials and by-products after the binding reaction of Example 7-2 and to purify the $^{17,65S}$G-CSF-PEG-Fc protein complex thus produced, the reaction mixture was passed through a Q HP (GE Healthcare, USA) anion exchange chromatography column and thus unbound Fc was removed and a $^{17,65S}$G-CSF-PEG-Fc protein complex fraction was obtained. The reaction solution was applied to a Q HP column equilibrated with 20 mM Tris (pH 8.0) buffer, and the $^{17,65S}$G-CSF-PEG-Fc protein complex was purified with a concentration gradient of a buffer solution containing 1 M sodium chloride (NaCl). A small amount of unreacted immunoglobulin Fc and $^{17,65S}$-CSF dimer as impurities was present in the obtained $^{17,65S}$G-CSF-PEG-Fc protein complex fraction. In order to remove the impurities, Source iso (GE Healthcare, USA) hydrophobic chromatography was further performed. Finally, a high-purity $^{17,65S}$G-CSF-PEG-Fc protein complex was purified with a linear concentration gradient of 50 mM Tris (pH 7.5) buffer solution containing 1.2 M ammonium sulfate using Source iso (GE Healthcare, USA). N-terminal selectivity of the Fc region of the prepared $^{17,65S}$G-CSF-PEG-Fc protein complex was examined by peptide mapping, and the selectivity was found to be 90% or higher.

Example 4: Preparation of Protein Complex Using PEG with Different Reactive Groups A FacVII-ATKAVC-PEG-Fc complex was prepared using FacVII-ATKAVC, which is a FacVII derivative of Korean Patent Application No. 10-2012-0111537 previously submitted by the present inventors.

4-1. Isolation and Purification of PEG-Fc Complex

First, to link an aldehyde reactive group of maleimide-10 kDa-PEG-aldehyde (NOF, Japan) to the N-terminus of immunoglobulin Fc fragment, the immunoglobulin Fc region and maleimide-10 kDa PEG-aldehyde were mixed at a molar ratio of 1:1 in a 100 mM phosphate buffer solution (pH 5.5 to 6.5), and a reducing agent, 20 mM sodium cyanoborohydride (NaCNBH3, Sigma), was added thereto under a protein concentration of 10 mg/mL. The reaction was allowed at a low temperature (4° C. to 8° C.) for about 2 hours. To obtain a monoPEGylated immunoglobulin Fc fragment (maleimide-10 kDa PEG-Fc), Source Q (GE Healthcare, USA) anion chromatography was performed, and elution was performed with a concentration gradient of sodium chloride in 20 mM Tris buffer at pH 7.5.

4-2. Preparation of FacVII-ATKAVC-PEG-Fc Complex

FacVII-ATKAVC was reacted in 10 mM glycylglycine buffer at pH 5.5 at room temperature for about 2 hours by adding 0.5 mM to 2 mM triphenylphosphine-3,3',3"-trisulfonic trisodium salt hydrate as a reducing agent so as to reduce the C-terminus. The C-terminus-reduced FacVII-ATKAVC and monoPEGylated immunoglobulin Fc fragment (maleimide-10 kDa PEG-Fc) were mixed at a molar ratio of 1:4 to 1:20, and reaction was allowed at a total protein concentration of 1 mg/mL to 2 mg/mL in 50 mM Tris buffer at pH 7.5 at room temperature for about 2 hours.

4-3. Isolation and Purification of FacVII-ATKAVC-PEG-Fc Complex

The reaction solution of Example 8-2 was subjected to Source Q anion chromatography, and the FacVII-ATKAVC-10 kDa PEG-Fc complex was eluted with a concentration gradient of sodium chloride in a 20 mM Tris buffer solution at pH 7.5. To activate FacVII of the FacVII-ATKAVC-PEG-Fc complex, reaction was allowed in a 0.1 M Tris-HCl buffer solution at pH 8.0 under conditions of about 4 mg/mL of FacVII for about 18 hours at a low temperature (4° C. to 8° C.). Finally, high-purity FacVIIa-ATKAVC-PEG-Fc was purified by size exclusion chromatography (GE Healthcare, USA) using Superdex 200 in a 10 mM glycylglycine buffer solution at pH 5.5. N-terminal selectivity of the Fc region of the prepared FacVIIa-ATKAVC-PEG-Fe protein complex was examined by peptide mapping, and the selectivity was found to be 90% or higher.

Example 5: Preparation of Protein Complex Using PEG with a Different Molecular Weight ALD-PEG-ALD (Nektar, USA), which is polyethylene glycol having a molecular weight of 10 kDa and aldehyde reactive groups at both ends thereof, was used to prepare and purify an insulin-10 kDa PEG conjugate in the same manner as in Example 5-2. The purified insulin-10 kDa PEG conjugate was concentrated to a concentration of about 5 mg/mL and then used to prepare and purify an insulin-10 kDa PEG-Fc protein complex in the same manner as in Example 2-3.

Example 6—Evaluation of Purity of Protein Complex 6-1. Identification of Protein Complex The protein complexes prepared in the above Examples were analyzed by non-reduced SDS-PAGE using a 4% to 20% gradient gel and a 12% gel. SDS-PAGE analysis and Western blot analysis of individual protein complexes using antibodies against immunoglobulin Fc and physiologically active polypeptides were performed. As shown in FIG. 1, a coupling reaction resulted in the successful production of IFNa-PEG-Fc (A), hGH-PEG-Fc (B), $^{17,65S}$G-CSF-PEG-Fc (C), Insulin-PEG-Fc (D), EPO-PEG-Fc (E), CA-Exendin4-PEG-Fc (F), and FacVII-PEG-Fc (G).

6-2. Evaluation of Purity of Protein Complex

The protein complexes prepared in the above Examples, IFNa-PEG-Fc (A), hGH-PEG-Fc (B), $^{17,65S}$ G-CSF-PEG-Fc (C), Insulin-PEG-Fc (D), EPO-PEG-Fc (E), and CA-Exendin4-PEG-Fc (F), were subjected to size exclusion chromatography, reverse phase chromatography, or ion exchange chromatography using HPLC, respectively. They displayed a single peak corresponding to high purity of 95% or higher in each analysis.

6-3. Examination of Site Selectivity of Protein Complex

The protein complexes prepared in Examples, IFNa-PEG-Fc (A), hGH-PEG-Fc (B), $^{17,65S}$ G-CSF-PEG-Fc (C), insulin-PEG-Fc (D), and EPO-PEG-Fc (E), were subjected to peptide mapping analysis (reverse phase chromatography) using protease, respectively. It was confirmed that the protein complexes linked via the N-terminus of the immunoglobulin Fc region with high selectivity of 90% or higher were prepared.

Example 7: Comparison of Efficacy of Complex Depending on Fc Binding Position The protein complexes prepared in Examples, CA-Exendin4-PEG-Fc, $^{17,65S}$G-CSF-PEG-Fc, and EPO-PEG-Fc, were subjected to in vitro and in vivo efficacy tests, respectively. As shown in the following Table, binding to the N-terminus (proline) of Fc showed better efficacy than binding to other regions (e.g., lysine).

TABLE 1 in vitro activity - CHO/GLP-1R bioassay of CAExendin-PEG-Fc positional isomers

| Test material | EC50 (ng/ml) | % vs. Experimental group |
|---|---|---|
| CA Exendin (lysine)-PEG-(N-terminus) Fc - Experimental group | 95.3 5 | 100.00 |
| CA Exendin (lysine)-PEG-(lysine) Fc | 59037 | 16.15 |

As shown in Table 1, comparison of in vitro activities between CA Exendin-PEG-Fc positional isomers showed that the CA Exendin-PEG-Fc complex of the present invention, which was prepared by specific binding to N-terminus of immunoglobulin Fc fragment, has 6 times higher potency than a CA Exendin-PEG-Fc complex which was prepared by binding to another position of an immunoglobulin Fc region.

TABLE 2 in vitro activity - use bone marrow cell proliferation assay of $^{17,65S}$G-CSF-PEG- Fc positional isomers

| Test material | EC50 (ng/ml) | % vs. Experimental group |
|---|---|---|
| $^{17,65S}$G-CSF- (N-terminus)-PEG-(N-Terminus) Fc-Experimental Group | 134.43 | 100.00 |
| $^{17,65S}$G-CSF- (N-terminus)-PEG-(lysine) Fc | 225.87 | 59.50 |

As shown in Table 2, comparison of in vitro activities between $^{17,65S}$G-CSF-(N-terminus)-PEG-(N-Terminus) Fc-Experimental Group S-G-CSF-PEG-Fc positional isomers showed that the $^{17,65S}$G-CSF-(N-terminus)-PEG-(N-Terminus) Fc-Experimental Group S-G-CSF-PEG-Fc complex of the present invention, which was prepared by specific binding to a N-terminus of immunoglobulin Fc fragment, has about 67% increased titer, compared to a $^{17,65S}$G-CSF-(N-terminus)-PEG-(N-Terminus) Fc-Experimental Group S-G-CSF-PEG-Fc complex which was prepared by binding to another position of an immunoglobulin Fc region.

Meanwhile, to examine in vivo activities of the protein complex of the present invention, in particular, EPO-PEG-Fc positional isomers, a normocythemic mice assay was performed to measure reticulocyte levels after subcutaneous injection of EPO-PEG-Fc into normocythemic mice.

TABLE 3

Measurement of in vivo bio-potency reticulocyte level of EPO-PEG-Fc positional isomers (after subcutaneous injection into nonnocythemic mice).

| Test material | Bio-potency (IU/mg) | % vs. Experimental group |
|---|---|---|
| EPO (N-terminus 84.4%)PEG-(N-Terminus 100%) Fc-Experimental Group | 14,189,403 | 100.00 |
| EPO (N-terminus 38.2%)-PG-(lysine 83.0%) Fc | 225.87 | 59.50 |

As shown in Table 3, comparison of in vivo activities between EPO-PEG-Fc positional isomers showed that the EPO-PEG-Fc complex of the present invention, which was prepared by specific binding to N-terminus of immunoglobulin Fc fragment, has about 40% increased titer, compared to an EPO-PEG-Fc complex which was prepared by binding to another position of an immunoglobulin Fc region.

These results suggest that when the protein complex comprising the physiologically active polypeptide, the non-peptidyl polymer, and the immunoglobulin Fc region is prepared by using a specific site of the immunoglobulin Fc fragment as a binding site, the protein complex shows an improved in vivo activity of the physiologically active polypeptide.

Example 8: Randomized Human Trial $^{17,65S}$G-CSF-PEG-Fc Protein Complex (EFLAPEGRASTIM) Vs. PEGFILGRASTIM in the Management of Chemotherapy-Induced Neutropenia in Breast Cancer Patients Receiving Docetaxel and Cyclophosphamide (TC)

To evaluate the efficacy and safety of a fixed dose of EFLAPEGRASTIM (13.2 mg/0.6 mL; 3.6 mg GCSF equivalent) in patients with breast cancer who were candidates for adjuvant or neoadjuvant chemotherapy with docetaxel and cyclophosphamide (TC), open-label, active-controlled, human studies were conducted in 406 patients.

Eligible patients were randomized 1:1 to the following two treatment arms: (a) EFLAPEGRASTIM Arm: EFLAPEGRASTIM 13.2 mg/0.6 mL (containing 3.6 mg G-CSF) fixed dose and (b) PEGFILGRASTIM Arm: PEGFILGRASTIM 6 mg/0.6 mL (containing 6.0 mg G-CSF) fixed dose. Accordingly, TC was administered on Day 1 of each cycle intravenously (IV) was: (i) Docetaxel at 75 mg/m$^2$ IV infusion per institute's standard of care (ii) Cyclophosphamide 600 mg/m$^2$ IV infusion per institute's standard of care. Each treatment cycle was 21 days with up to a maximum of 4 cycles of chemotherapy. To begin full-dose chemotherapy on Day 1 of any cycle (Day 22 of the previous cycle), patients must have ANC≥1.5×10$^9$/L and a platelet count≥100×10$^9$/L.

EFLAPEGRASTIM or PEGFILGRASTIM were administered on Day 2 of each cycle, approximately 24 hours (±2 hours) after TC chemotherapy. PEGFILGRASTIM was to be administered according to the manufacturer's Prescribing Information (6 mg subcutaneously once per chemotherapy cycle).

Patients meeting all inclusion and exclusion criteria were randomized to either the EFLAPEGRASTIM Arm or the PEGFILGRASTIM Arm and received study treatment (TC) followed 24 (±2) hours by either EFLAPEGRASTIM or PEGFILGRASTIM for 4 cycles. End of treatment (EOT) visits were performed 35 (±5) days from the last dose of study treatment. During Cycle 1, CBC samples were drawn on Day 1 prior to the chemotherapy and then daily from Days 4 to 15 or until recovery from neutropenia. In Cycles 2 to 4, CBC samples were drawn on Day 1 predose and then on Days 4, 7, 10 and 15 (±1 day for each collection). CBC was also collected at the End-of-Treatment Visit. Sparse PK samples for population PK were collected in Cycle 1 on Day 2, Day 4, and Day 5 and then in Cycle 3 on Day 2, Day 4, and Day 7. Immunogenicity samples were drawn at each cycle before chemotherapy administration, at the end of treatment, and at 6 and 12 months (long term safety).

Figure 3:
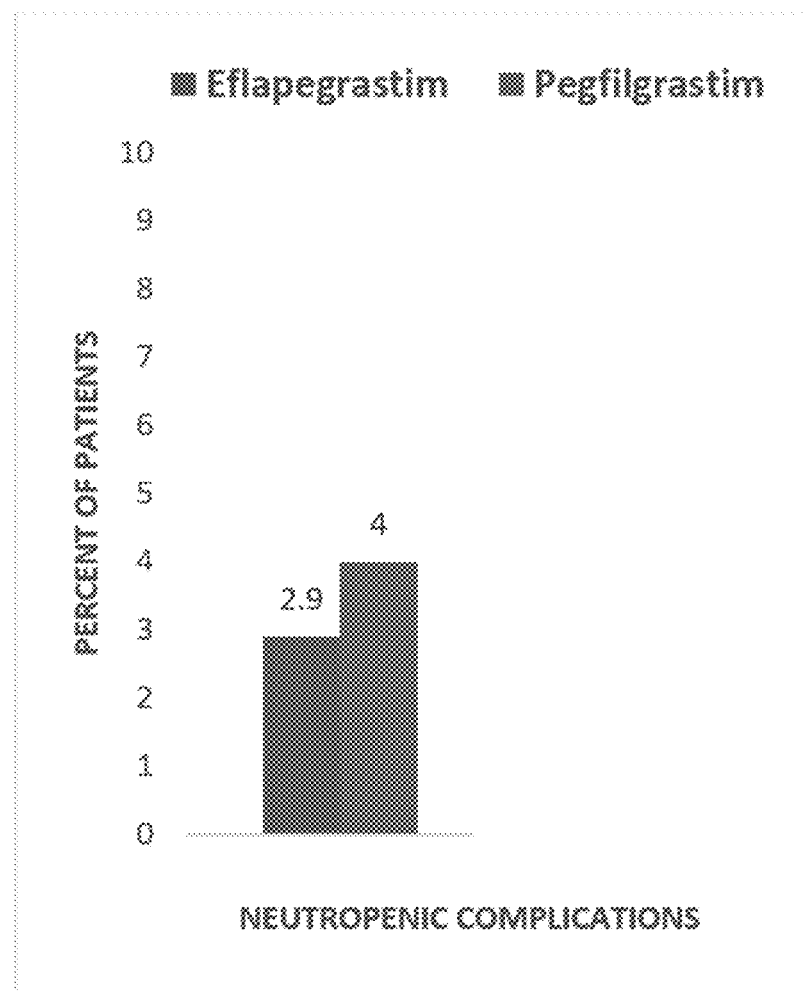
FIG. 3 shows that neutropenic complications, including hospitalizations due to severe neutropenia and/or use of anti-infective for neutropenia, are significantly less in the EFLAPEGRASTIM arm.

Patients who received at least one dose of study drug and did not discontinue from the study are being followed for long term safety after the last dose of study treatment. The long-term safety includes adverse event (AE) assessment via telephone at 3 months and 9 months and clinic visits for AE assessment and immunogenicity blood draw at 6 months and 12 months. The DSN in Cycle 1 is defined as the number of postdose days of severe neutropenia Efficacy analysis was conducted for the primary endpoint of the Duration of Severe neutropenia (DSN) in Cycle 1 defined as the number of postdose days of severe neutropenia (ANC<0.5×10$^9$/L) from the first occurrence of an ANC below the threshold. The results showed that the mean DSN for the EFLAPEGRASTIM Arm was 0.20 (±0.50) days compared with a mean DSN of 0.35 (±0.68) days in the PEGFILGRASTIM Arm. The difference in mean DSN between the EFLAPEGRASTIM Arm and the PEGFILGRASTIM Arm was −0.15 days and the corresponding 95% CI was (−0.264, −0.032) using the percentile method as specified in the statistical analysis plan. Using the pre-specified criterion for the primary endpoint, the EFLAPEGRASTIM Arm to the PEGFILGRASTIM Arm was demonstrated to provide non-inferior DSN (better or as effective) as PEGFILGRASTIM (upper bound of 95% CI<0.62 days; p<0.0001). The results also demonstrated a statistical superiority of EFLAPEGRASTIM over PEGFILGRASTIM in cycle 1 (upper bound of 95% CI<0; p=0.038) indicating that the incidence of severe neutropenia is significantly lower in EFLAPEGRASTIM arm (FIG. 2 and FIG. 3). In the meantime, the incidences of adverse events were in general comparable between treatment groups, most of which were considered relating to the chemotherapy (TC) administration.

The Examples provided herein supports the superiority of the G-CSF protein complex attached the immunoglobulin Fc region through a PEG moiety to increase in vivo duration of the physiologically active polypeptide and to increase or maintain in vivo activity (potency) at the same time.

Based on the above description, it will be understood by those skilled in the art that the present invention may be implemented in a different specific form without changing the technical spirit or essential characteristics thereof. Therefore, it should be understood that the above embodiment is not limitative, but illustrative in all aspects. The scope of the invention is defined by the appended claims rather than by the description preceding them, and therefore all changes and modifications that fall within metes and bounds of the claims, or equivalents of such metes and bounds, are therefore intended to be embraced by the claims.

What is claimed is:

1. A method of preventing, alleviating, or treating neutropenia in a patient having compromised white blood cell production comprising administering to the patient a therapeutically effective amount of a protein complex comprising a modified human granulocyte-colony stimulating factor (hG-CSF) covalently linked to an immunoglobulin Fc region via a non-peptidyl polymer, wherein the non-peptidyl polymer is site-specifically linked to an N-terminus of the immunoglobulin Fc region and the modified hG-CSF comprises the amino acid sequence of SEQ ID NO: 1.

2. The method of claim 1, wherein the neutropenia is severe chronic neutropenia or febrile neutropenia.

3. The method of claim 1, wherein said compromised white blood cell production is a result of chemotherapy, radiation therapy, or idiopathic thrombocytopenia purpura.

4. The method of claim 1, wherein the protein complex is administered after the patient is treated with adjuvant or neoadjuvant chemotherapy.

5. The method of claim 4, wherein the protein complex is administered between 1 and 5 days after the patient is treated with adjuvant or neoadjuvant chemotherapy.

6. The method of claim 5, wherein the adjuvant or neoadjuvant chemotherapy is a combination of docetaxel and cyclophosphamide.

7. The method of claim 1, wherein a second dose of the protein complex is administered between 15 and 25 days after a first dose of the protein complex is administered to the patient.

8. The method of claim 1, wherein the therapeutically effective amount is a unit dosage form selected from: 25 µg/kg, 50 µg/kg, 100 µg/kg, and 200 µg/kg.

9. The method of claim 1, wherein the therapeutically effective amount is 13.2 mg of the protein complex in a 0.6 mL dosage volume.

10. The method of claim 1, further comprising administering to the patient a therapeutically effective amount of a second agent.

11. The method of claim 10, wherein the second agent is an anti-cancer agent.

12. The method of claim 1, wherein the immunoglobulin Fc region comprises a polypeptide sequence of SEQ ID NO: 2.

13. The method of claim 12, wherein both ends of the non-peptidyl polymer are respectively linked to the modified human G-CSF and the immunoglobulin Fc region through reactive groups by a covalent bond.

14. The method of claim 13, wherein the reactive group of the non-peptidyl polymer is an aldehyde group.

15. The method of claim 14, wherein:
(a) the aldehyde group is a propionaldehyde group or a butyraldehyde group; or
(b) the succinimide derivative is succinimidyl carboxymethyl, succinimidyl valerate, succinimidyl methylbutanoate, succinimidyl methylpropionate, succinimidyl butanoate, succinimidyl propionate, N-hydroxysuccinimide, or succinimidyl carbonate.

16. The method of claim 14, wherein:
(a) the non-peptidyl polymer has an aldehyde group as a reactive group at both ends;
(b) the non-peptidyl polymer has an aldehyde group and a maleimide group as a reactive group at both ends, respectively; or
(c) the non-peptidyl polymer has an aldehyde group and a succinimide group as a reactive group at both ends, respectively.

17. The method of claim 1, wherein the immunoglobulin Fc region consists of CH2 and CH3 domains.

18. The method of claim 17, wherein the immunoglobulin Fc fragment is an IgG4 Fc fragment.

19. The method of claim 1, wherein the non-peptidyl polymer is polyethylene glycol.

20. The method of claim 19, wherein the polyethylene glycol has a molecular weight of 3.4 kDa.

21. The method of claim 1, wherein each end of the non-peptidyl polymer is linked to the N-terminus of the immunoglobulin Fc region and an N-terminus, a C-terminus, or a free reactive group of a lysine residue, a histidine residue, or a cysteine residue of the modified human G-CSF, respectively.

* * * * *